United States Patent
Adams et al.

(10) Patent No.: US 6,544,271 B1
(45) Date of Patent: Apr. 8, 2003

(54) DEVICE FOR FULL-THICKNESS RESECTIONING OF AN ORGAN

(75) Inventors: Ronald D. Adams, Holliston, MA (US); Roy H. Sullivan, Millville, MA (US); Gerhard F. Buess, Tubingen Bebenhausen (DE); Marc O. Schurr, Tuebingen (DE)

(73) Assignee: SciMed Life Systems, Inc., Maple Grove, MN (US)

( * ) Notice: Subject to any disclaimer, the term of this patent is extended or adjusted under 35 U.S.C. 154(b) by 312 days.

(21) Appl. No.: 09/620,391

(22) Filed: Jul. 18, 2000

(51) Int. Cl.⁷ .................................................. A61B 17/10
(52) U.S. Cl. ........................ 606/139; 606/75; 606/151
(58) Field of Search ............................... 606/219, 220, 606/72, 75, 215, 167, 170

(56) References Cited

U.S. PATENT DOCUMENTS

| | | |
|---|---|---|
| 2,905,178 A | 9/1959 | Hilzinger, III |
| 3,193,165 A | 7/1965 | Akhalaya et al. |
| 3,388,847 A | 6/1968 | Kasulin et al. |
| 3,452,615 A | 7/1969 | Gregory, Jr. |
| 3,552,626 A | 1/1971 | Astafiev et al. |
| 3,638,652 A | 2/1972 | Kelley |
| 3,952,747 A | 4/1976 | Kimmell, Jr. |
| 4,108,211 A | 8/1978 | Tanaka |
| 4,198,982 A | 4/1980 | Fortner et al. |
| 4,207,898 A | 6/1980 | Becht |
| 4,304,236 A | 12/1981 | Conta et al. |
| 4,319,576 A | 3/1982 | Rothfuss |
| 4,351,466 A | 9/1982 | Noiles |
| 4,466,436 A * | 8/1984 | Lee .......................... 227/179.1 |
| 4,473,077 A | 9/1984 | Noiles et al. |
| 4,485,817 A | 12/1984 | Swiggett |
| 4,488,523 A | 12/1984 | Shichman |
| 4,505,272 A | 3/1985 | Utyamyshev et al. |

(List continued on next page.)

FOREIGN PATENT DOCUMENTS

| | | |
|---|---|---|
| FR | 2 768 324 | 3/1999 |
| GB | 1185292 | 3/1970 |
| GB | 2 347 418 | 4/1974 |
| GB | 2016 991 A | 10/1979 |
| GB | 2 038 692 A | 7/1980 |
| WO | 96/18344 | 6/1996 |
| WO | WO 97/47231 | 12/1997 |

OTHER PUBLICATIONS

Pietrafitta et al., "Experimental Transperitoneal Laparoscopic Pyloroplasty," Surgical Laparoscopy & Endoscopy, vol. 2, No. 2, 1992, pp. 104–110.

*Primary Examiner*—Michael J. Milano
*Assistant Examiner*—P Roberts
(74) *Attorney, Agent, or Firm*—Fay Kaplun & Marcin, LLP

(57) ABSTRACT

A full-thickness resection system is disclosed. In an embodiment for the resection system, the system may include a flexible shaft, a flexible guide member disposed within the flexible shaft, a stapling mechanism disposed around the flexible guide member, and a grasper. The stapling mechanism has an elongated portion that is at least partially disposed within the flexible shaft. The stapling mechanism includes a stapling arm and an anvil arm. The stapling arm has a longitudinal axis and includes a stapling head having a longitudinal axis. The anvil includes an anvil head. The stapling arm and anvil arm extend from the elongated portion of the stapling mechanism and are moveable with respect to each other between a tissue receiving position and a stapling position. The grasper extends through the flexible shaft and is adapted to grasp a portion of a tissue that is to be excised from an organ in the patient's body. The grasper is movable on an axis that is perpendicular to the longitudinal axis of the stapling head.

27 Claims, 16 Drawing Sheets

U.S. PATENT DOCUMENTS

| | | | |
|---|---|---|---|
| 4,505,414 A | | 3/1985 | Filipi |
| 4,573,468 A | | 3/1986 | Conta et al. |
| 4,576,167 A | | 3/1986 | Noiles |
| 4,592,354 A | | 6/1986 | Rothfuss |
| 4,603,693 A | | 8/1986 | Conta et al. |
| 4,606,343 A | | 8/1986 | Conta et al. |
| 4,610,383 A | | 9/1986 | Rothfuss et al. |
| 4,617,928 A | | 10/1986 | Alfranca |
| 4,667,673 A | | 5/1987 | Li |
| 4,671,445 A | | 6/1987 | Barker et al. |
| 4,752,024 A | | 6/1988 | Green et al. |
| 4,874,122 A | * | 10/1989 | Froelich et al. ............... 227/19 |
| 4,893,622 A | | 1/1990 | Green et al. |
| 4,957,499 A | | 9/1990 | Lipatov et al. |
| 5,014,899 A | | 5/1991 | Presty et al. |
| 5,100,419 A | | 3/1992 | Ehlers |
| 5,122,156 A | | 6/1992 | Granger et al. |
| 5,139,513 A | | 8/1992 | Segato |
| 5,158,222 A | | 10/1992 | Green et al. |
| 5,193,731 A | | 3/1993 | Aranyi |
| 5,197,648 A | | 3/1993 | Gingold |
| 5,197,649 A | | 3/1993 | Bessler et al. |
| 5,205,459 A | | 4/1993 | Brinkerhoff et al. |
| 5,222,963 A | | 6/1993 | Brinkerhoff et al. |
| 5,236,440 A | * | 8/1993 | Hlavacek .................... 128/898 |
| 5,254,129 A | * | 10/1993 | Alexander .................. 30/135 |
| 5,261,920 A | | 11/1993 | Main et al. |
| 5,269,769 A | * | 12/1993 | Dhara et al. ........... 128/207.14 |
| 5,271,543 A | | 12/1993 | Grant et al. |
| 5,271,544 A | | 12/1993 | Fox et al. |
| 5,282,810 A | | 2/1994 | Allen et al. |
| 5,285,944 A | | 2/1994 | Green et al. |
| 5,285,945 A | | 2/1994 | Brinkerhoff et al. |
| 5,292,053 A | | 3/1994 | Bilotti et al. |
| 5,309,927 A | | 5/1994 | Welsch |
| 5,314,435 A | | 5/1994 | Green et al. |
| 5,314,436 A | | 5/1994 | Wilk |
| 5,330,486 A | | 7/1994 | Wilk |
| 5,333,773 A | | 8/1994 | Main et al. |
| 5,344,059 A | | 9/1994 | Green et al. |
| 5,350,104 A | | 9/1994 | Main et al. |
| 5,355,897 A | | 10/1994 | Pietrafitta et al. |
| 5,360,154 A | | 11/1994 | Green |
| 5,368,215 A | | 11/1994 | Green et al. |
| 5,373,854 A | * | 12/1994 | Kolozsi ..................... 600/562 |
| 5,389,098 A | | 2/1995 | Tsuruta et al. |
| 5,392,979 A | | 2/1995 | Green et al. |
| 5,395,030 A | | 3/1995 | Kuramoto et al. |
| 5,395,034 A | | 3/1995 | Allen et al. |
| 5,403,326 A | * | 4/1995 | Harrison et al. ............. 128/898 |
| 5,411,508 A | | 5/1995 | Bessler et al. |
| 5,425,738 A | | 6/1995 | Gustafson et al. |
| 5,433,721 A | | 7/1995 | Hooven et al. |
| 5,437,684 A | | 8/1995 | Calabrese et al. |
| 5,439,156 A | | 8/1995 | Grant et al. |
| 5,441,507 A | | 8/1995 | Wilk |
| 5,443,198 A | | 8/1995 | Viola et al. |
| 5,445,644 A | | 8/1995 | Pietrafitta et al. |
| 5,447,514 A | | 9/1995 | Gerry et al. |
| 5,454,825 A | | 10/1995 | Van Leeuwen et al. |
| 5,465,895 A | | 11/1995 | Knodel et al. |
| 5,474,223 A | | 12/1995 | Viola et al. |
| 5,478,354 A | * | 12/1995 | Tovey et al. ................. 411/457 |
| 5,485,947 A | | 1/1996 | Olson et al. |
| 5,485,952 A | | 1/1996 | Fontayne |
| 5,522,534 A | | 6/1996 | Viola et al. |
| 5,527,331 A | * | 6/1996 | Kresch et al. ................ 604/22 |
| 5,533,661 A | | 7/1996 | Main et al. |
| 5,554,164 A | * | 9/1996 | Wilson et al. ................ 227/19 |
| 5,571,116 A | | 11/1996 | Bolanos et al. |
| 5,609,285 A | | 3/1997 | Grant et al. |
| 5,749,893 A | | 5/1998 | Vidal et al. |
| 5,826,776 A | * | 10/1998 | Schulze et al. .......... 227/176.1 |
| 5,855,311 A | * | 1/1999 | Hamblin et al. ......... 227/176.1 |
| 5,868,760 A | | 2/1999 | McGuckin, Jr. |
| 5,893,506 A | * | 4/1999 | Powell .................... 227/175.1 |
| 6,001,116 A | * | 12/1999 | Heisler et al. .............. 606/170 |
| 6,068,639 A | * | 5/2000 | Fogarty et al. ............. 128/898 |
| 6,086,600 A | | 7/2000 | Kortenbach |
| 6,159,209 A | * | 12/2000 | Hakky ......................... 604/22 |
| 6,302,311 B1 | * | 10/2001 | Adams et al. ........... 227/176.1 |

\* cited by examiner

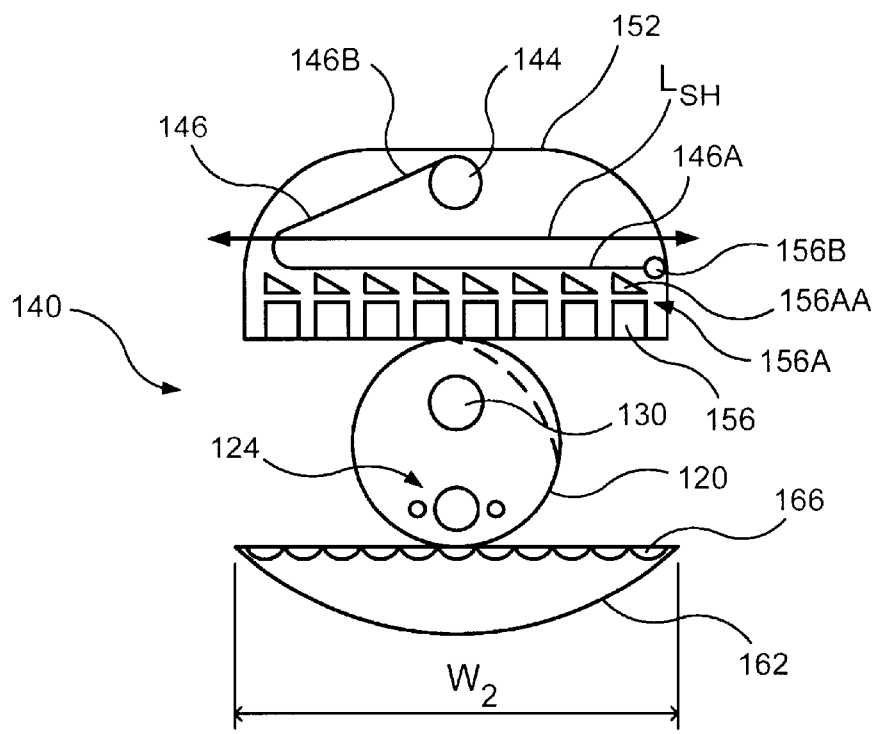
F I G. 2
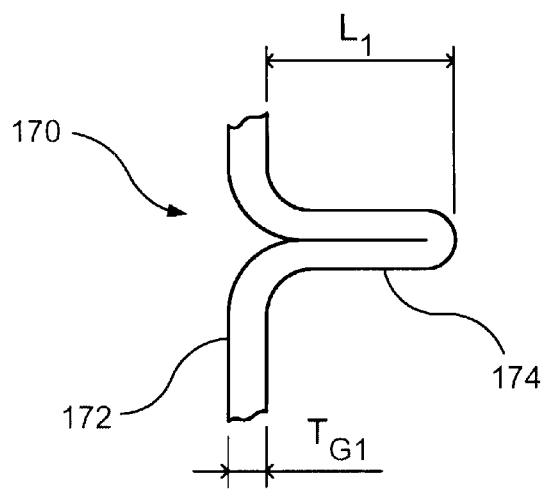
F I G. 3

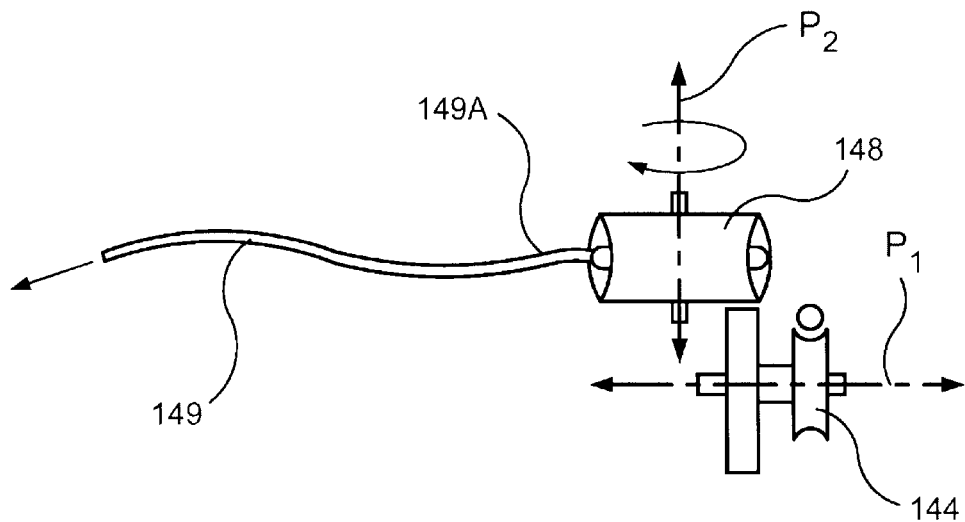
F I G. 4
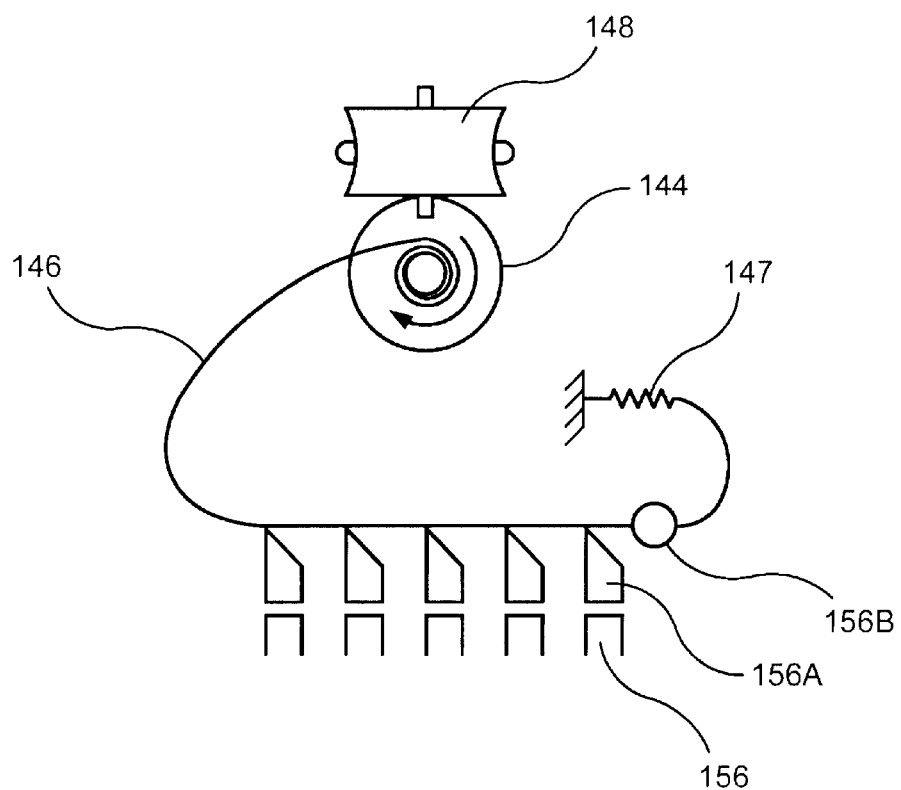
F I G. 5

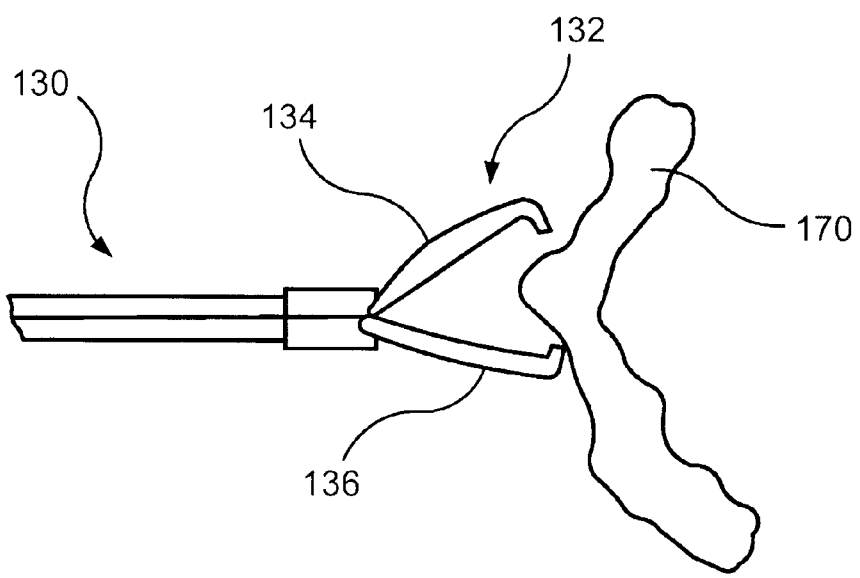
F I G. 6
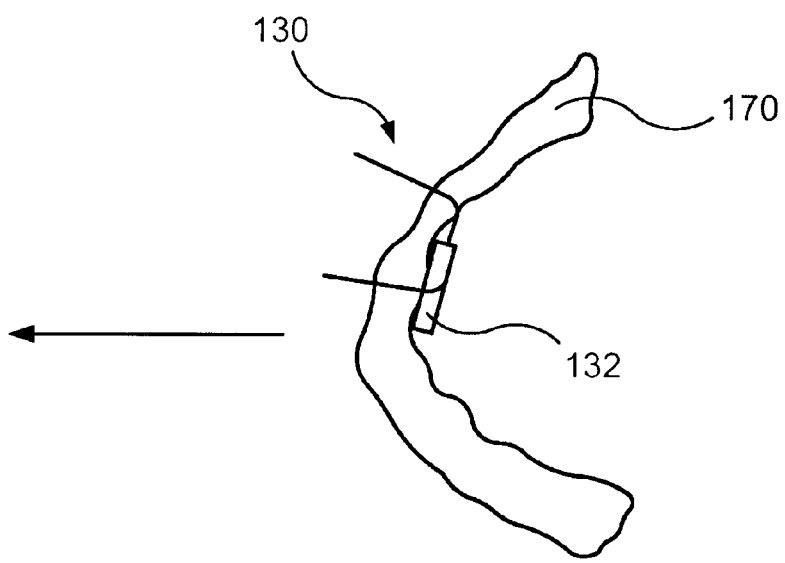
F I G. 7

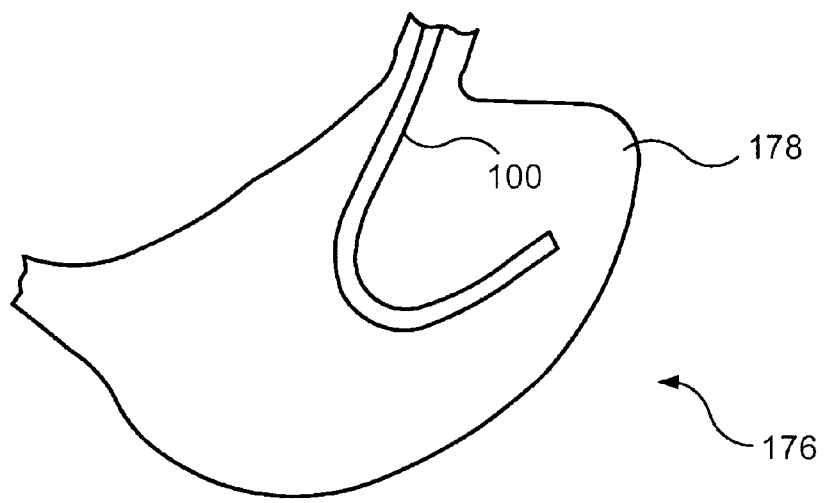
F I G. 8
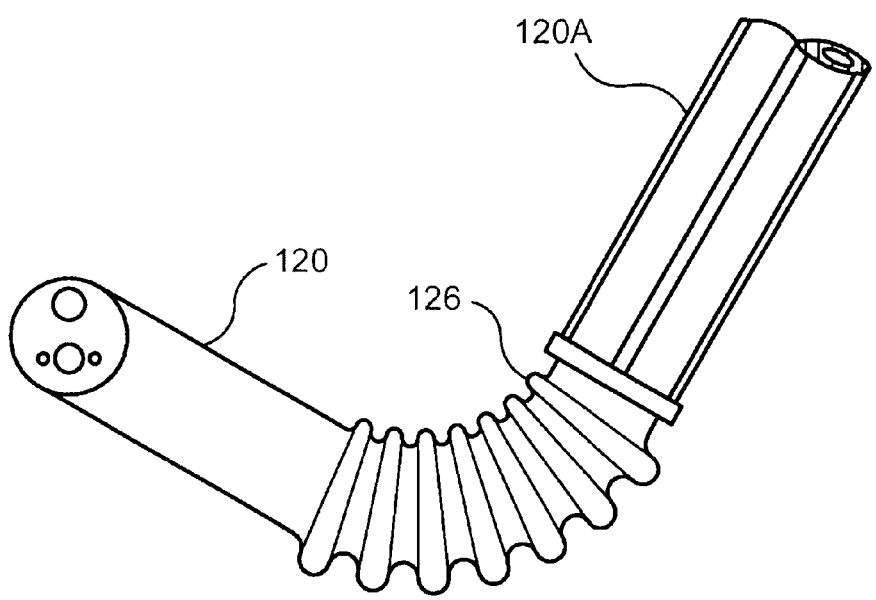
F I G. 9

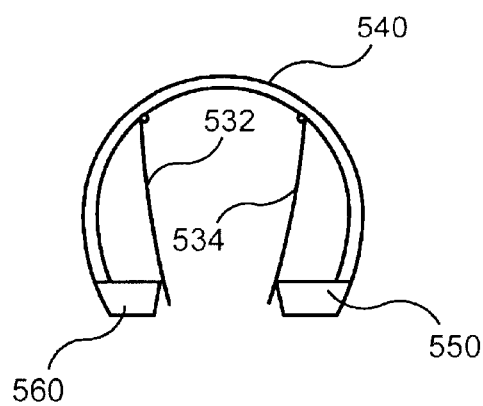
F I G. 20
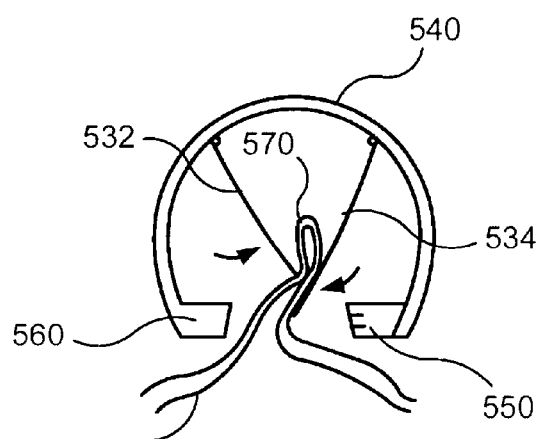
F I G. 21
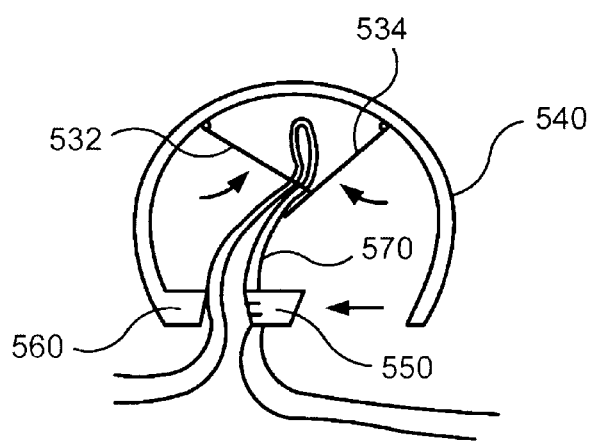
F I G. 22

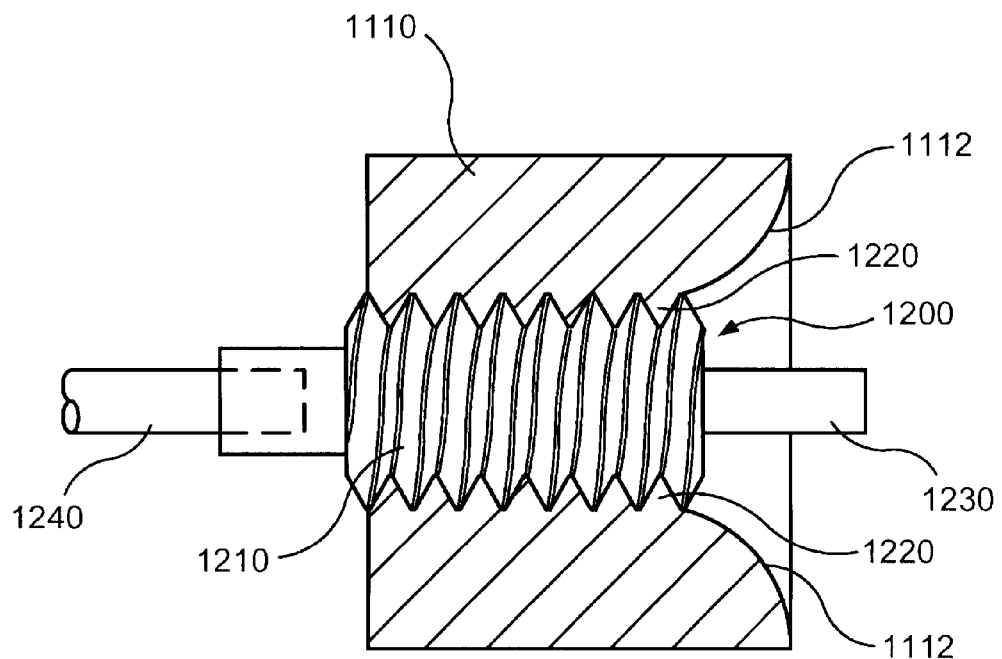
F I G. 24

DEVICE FOR FULL-THICKNESS RESECTIONING OF AN ORGAN

BACKGROUND OF THE INVENTION

1. Field of the Invention

The present invention relates to full thickness resection devices for performing localized resections of lesions in body organs, particularly gastric lesions.

2. Description of the Related Art

A resection procedure involves excising a portion of an organ, approximating the surrounding tissue together to close up the hole created by the excision, and removing the excess tissue. Various conventional devices and procedures are known for resectioning lesions in body organs, however, known resection devices suffer deficiencies. Some of these deficiencies with known devices include: the lack of a capability to view the lesion within the body and to grasp the lesion to position the lesion within the resection device; they require abdominal wall penetrations; and they have sizes and structures, e.g., rigid rather than flexible, that are not desirable.

As mentioned above, many known resection devices and procedures require at least one incision in an area near the portion of the organ that is to be excised. This incision may be required to allow the physician to gain access to the lesion, to view the lesion during the procedure, and to provide an opening in the body cavity large enough such that the surgeon is able to perform all of the required steps of the procedure with all of the variety of different surgical instruments required. It is not desirable to require an incision for performing the resection procedure. When an incision is required, the patient must receive general anesthesia, and thus, the procedure cannot be performed on an outpatient basis which would require only conscious sedation. Additionally, the incision results in pain for the patient during the recuperation period and may involve a partial or entire loss of mobility while recuperating from the incision. Thus, the time required to recover from such a procedure is often longer than for procedures which do not require incisions.

To attempt to overcome some of the deficiencies noted above, a known resection device includes an endoscope and a surgical stapling and cutting apparatus for resectioning lumenal tissue. Whereas this device may obviate the requirement for percutaneous access to the lesion site, drawbacks exist with this resection device, particularly if utilized for excision of gastric lesions. The resection device includes a circular, or semi-circular, stapling instrument. Whereas circular stapling devices are useful for resectioning tubular organs, such as a colon, they have deficiencies if used for resectioning gastric lesions.

Circular staplers are optimally suited for resectioning tubular organs, such as the colon. The colon is comprised of a generally tubular, thin-walled structure. When a section of tissue is removed from the wall of the tubular organ, the circularly-shaped stapler is best-suited for joining the curved wall surfaces that define the hole in the wall that results when the tissue section is removed. By positioning the staples in a circular orientation in the tubular wall structure, when contrasted with positioning the staples in a linear orientation, a minimal obstruction will result within the internal smooth bore of the tubular organ.

However, it is not advantageous to utilize a circularly-shaped resection device for resectioning gastric lesions. The walls of the stomach are formed much differently than those of tubular organs. Whereas the tubular organs are generally thin-walled structures, the stomach is generally formed by thick-walled, multi-layered, flat, muscle tissue. Resectioning of the stomach is generally accomplished by removing a three-sided wedge-shaped portion of the stomach wall. Three linear cuts are made in the stomach wall to form the wedge portion to be removed and, thus, it is desirable to staple the stomach wall along the same axes as those on which the cuts were made. This cannot be accomplished if a circular stapler is utilized. Circular staplers are limited by the area circumscribed by the circular area within the staple/line cut. Utilizing a circular stapler to resection tissue that is linearly cut would be akin to utilizing a circular hole punch to cut-out a triangular wedge shape in a piece of paper rather than utilizing scissors to cut the wedge shape. Utilizing a linear stapler would give the freedom to remove much larger areas via a series of extended cuts.

Additionally, if a circular stapler was used to resection the gastric wall, positioning of the stapler would be difficult. Circular staplers are generally orientated within the resection device around a center post. If a circular stapler was used to resection tissue on the generally flat wall of the stomach, to properly position the stapler around the lesion, the center post would contact, and thus possibly puncture, the lesion. This is not clinically desirable and could result in complications for the patient. Thus, whereas a circular stapler resectioning device may obviate the requirement for an incision when performing resectioning procedures on tubular organs, the device has drawbacks, particularly if utilized to resection gastric lesions.

An additional problem with known resection devices is difficulty in properly positioning the tissue to be removed within the device. This problem is particularly apparent in procedures involving the gastric wall. As stated above, the gastric wall comprises thick, multi-layered, muscle tissue. This is in stark contrast to the generally thin-walled tubular organs. Thus, the stomach tissue is much more difficult to draw into the resection device than is the tissue of tubular organs.

In order to draw the tissue into the resection device, many known procedures require the use of a separate tool(s) to grasp the tissue and position it within the resection device. This has the obvious drawbacks of requiring the physician to insert and utilize a separate tool(s) for grasping and manipulating the tissue. This results in additional complexity for the procedure and may require a larger incision, or multiple incisions, into the patient so that the ancillary tool(s) may be inserted into the patient's body.

Even if a grasper tool is incorporated into a resection device, such known resection devices, even if they could be utilized to cut and staple the stomach tissue, would not able to adequately position the uniquely difficult gastric wall within the device. The grasper most probably is not structurally sufficient to manipulate the more difficult to maneuver thicker gastric wall. Additionally, in a colonic procedure with a circular stapler, the pulling direction may be parallel to the stapler axis. However, in a gastric procedure, it is not desirable that the pulling direction be parallel to the staple line since this could create wrinkles of tissue in the edges of the linear staple line.

Therefore, it would be desirable to provide an improved method and apparatus for performing localized resections of lesions in body organs, particularly gastric lesions.

SUMMARY OF THE INVENTION

A full-thickness resection system is provided. In an embodiment for the resection system, the system may include a flexible shaft, a flexible guide member disposed within the flexible shaft, a stapling mechanism disposed around the flexible guide member, and a grasper. The stapling mechanism has an elongated portion that is at least partially disposed within the flexible shaft. The stapling mechanism includes a stapling arm and an anvil arm. The stapling arm has a longitudinal axis and includes a stapling head having a longitudinal axis. The anvil includes an anvil head. The stapling arm and anvil arm extend from the elongated portion of the stapling mechanism and are moveable with respect to each other between a tissue receiving position and a stapling position. The grasper extends through the flexible shaft and is adapted to grasp a portion of a tissue that is to be excised from an organ in the patient's body. The grasper is movable on an axis that is perpendicular to the longitudinal axis of the stapling head.

BRIEF DESCRIPTION OF THE DRAWINGS

FIG. 2 is a front view of the full-thickness resection system of FIG. 1.

FIG. 3 is a side view of a section of a gastric wall that may be resectioned by utilizing the full-thickness resection system of the present invention.

FIG. 4 is a side view of a first embodiment for a staple driver actuator in accordance with the present invention.

FIG. 5 is a front view of the staple driver actuator of FIG. 4.

FIG. 6 illustrates a first embodiment for a grasper in accordance with the present invention.

FIG. 7 illustrates a second embodiment for a grasper in accordance with the present invention.

FIG. 8 illustrates the positioning of a full-thickness resection system in the stomach of a patient.

FIG. 9 illustrates a flexible endoscope assembly in accordance with the present invention.

FIG. 20 is a front view of the resection system of FIG. 19 with the wings of a grasper in a tissue receiving position.

FIG. 21 is a front view of the resection system of FIG. 19 with the wings grasping the tissue to be resectioned.

FIG. 22 is a front view of the resection system of FIG. 19 with the stapling head and the anvil head drawn towards each other to resection the tissue.

FIG. 24 is a cross-sectional view of an embodiment of a closing cam actuating device.

DETAILED DESCRIPTION

Figure 1:
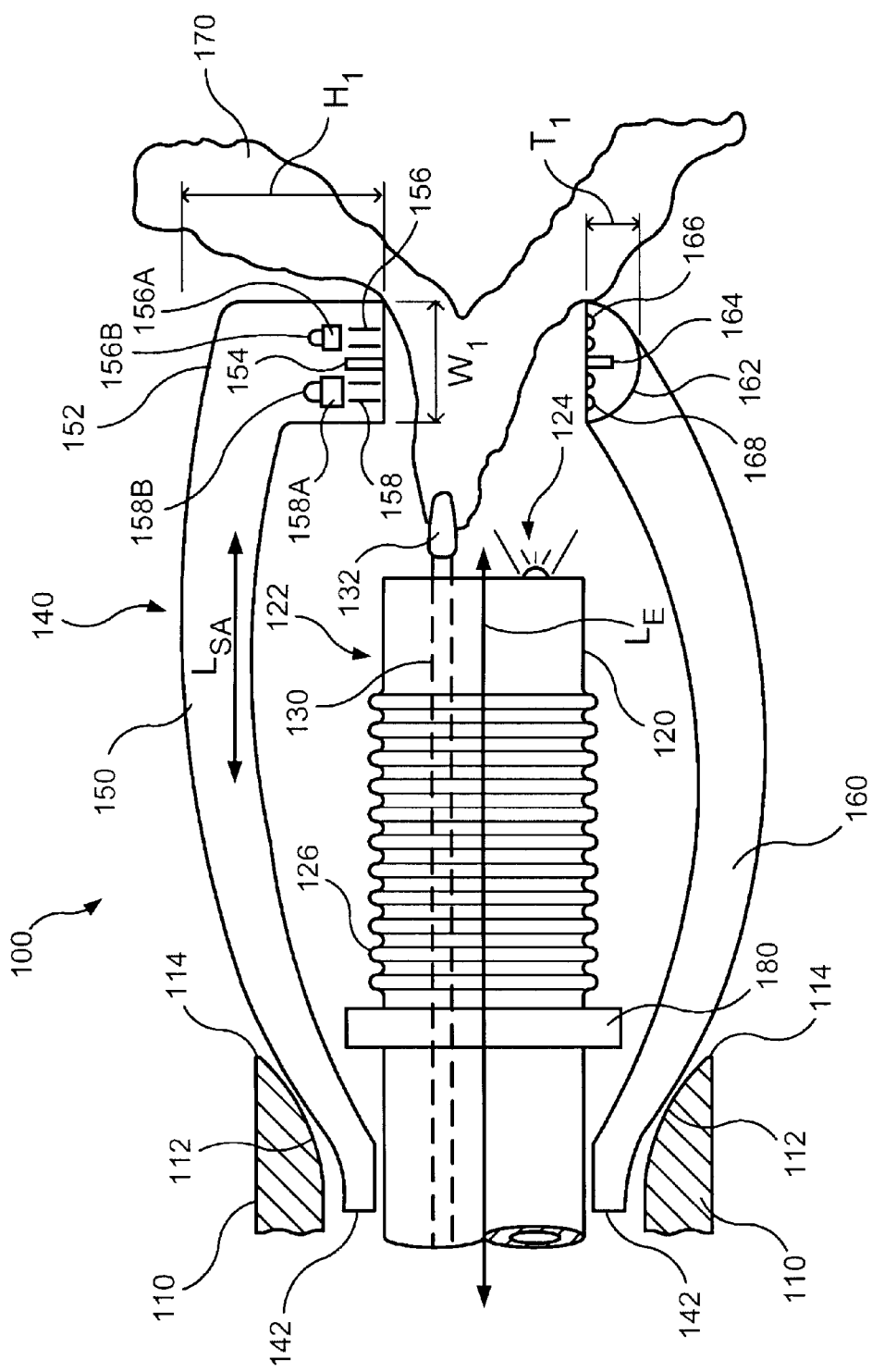
FIG. 1 is a side view of a first embodiment of a full-thickness resection system in accordance with the present invention.

FIG. 1 illustrates a first embodiment for a full-thickness resection system 100 in accordance with the present invention. As can be seen in FIG. 1, full-thickness resection system 100 may include a closing cam 110, which may be associated with and/or actuated by a flexible shaft, a grasper 130, and a stapling mechanism 140. A flexible guide member 120, which in this embodiment is a flexible endoscope, is included within full thickness resection system 100 and grasper 130 may extend through a lumen included in the flexible endoscope 120. A stop 180 may be included on flexible endoscope 120. Closing cam 110 may be included on the distal ends of the flexible shaft or may be movable within the flexible shaft. Stapling mechanism 140 includes a stapling arm 150, which also includes a stapling head 152, and an anvil arm 160, which includes an anvil head 162. Each of these components of full-thickness resection system 100 will be described in further detail below. In utilizing full-thickness resection system 100, which will also be described in further detail below, gastric wall tissue 170 is grasped by grasper 130 and is positioned between stapling head 152 and anvil head 162 of stapling mechanism 140 where the gastric wall tissue 170 may be resectioned by full-thickness resection system 100.

In further describing each of the components of an embodiment for full-thickness resection system 100, closing cam 110 extends proximally from a distal end 114 and stapling mechanism 140 and flexible endoscope 120 extend from distal end 114 of closing cam 110. Distal end 114 includes a cam surface 112 around the entire periphery of tubular closing cam 110. In an embodiment of the present invention, when an operator retracts stapling mechanism 140 further within distal end 114 of stationary closing cam 110, cam surface 112 contacts and engages stapling arm 150 and anvil arm 160 to drive the arms toward each other to clamp the tissue between the anvil and staple head and to provide a controlled staple gap. Alternative mechanisms for closing arms 150 and 160, and thus for actuating a movable closing cam 110, will be discussed later in this specification.

Flexible endoscope 120, in this embodiment for full-thickness resection system 100, extends within closing cam 110 and distal end 122 of flexible endoscope 120 extends beyond the distal end 114 of closing cam 110. Flexible endoscope 120 is movable within closing cam 110 such that it may be extended from distal end 114 of closing cam 110 and may be retracted into closing cam 110. Flexible endoscope 120 includes an optic 124 at its distal end 122 as is well-known in the art. Optic 124 should have a minimum focal length of approximately 8 mm such that the tissue 170 may be viewed during all steps of the resection procedure. Also included in flexible endoscope 120 is a bending section 126 which permits the distal end 122 of the endoscope 120 to bend relative to the longitudinal axis $L_E$ of the endoscope. In this embodiment, the longitudinal axis of the flexible shaft is parallel to the longitudinal axis of the endoscope. Bending section 126 may be structurally configured in any of a variety of configurations and the present invention is not limited to any particular structural configuration for bending section 126.

As was mentioned previously, grasper 130 may extend within a lumen that is contained within flexible endoscope 120 and is movable within that lumen such that a grasping portion 132 of grasper 130 may be extended from distal end 122 of endoscope 120. Grasper 130 and grasping portion 132 may be configured in any of a variety of different configurations and the present invention is not limited to any particular configuration. The purpose of grasping portion 132 of grasper 130 is to provide for grasping tissue 170 such that it may be positioned within stapling mechanism 140 such that the tissue may be resectioned. Various possible embodiments for the grasping portion of the grasper will be discussed later in this specification. Additionally, a grasper does not need to include physical structure for grasping tissue, rather the grasper may be a suction catheter where a suction drawn through the catheter grasps the tissue.

As was mentioned above, stapling mechanism 140 includes a stapling arm 150 and an anvil arm 160. In this embodiment, included at a distal end of stapling arm 150 is a stapling head 152 and included at a distal end of anvil arm 160 is an anvil head 162. Stapling head 152 and anvil head 162 will be described further below. Stapling arm 150 and anvil arm 160 extend from an elongated portion 142 of stapling mechanism 140. Elongated portion 142 extends, at least partially, within closing cam 110. As was mentioned previously, as elongated portion 142 is moved within closing cam 110, stapling arm 150 and anvil arm 160 will engage with cam surface 112 such that stapling head 152 and anvil head 162 are brought together such that the tissue to be resectioned may be cut with a knife and joined by staples included in stapling mechanism 140. Any variety of different structures and methods may be utilized for withdrawing elongated portion 142 further within closing cam 110 such that stapling arm 150 and anvil arm 160 are drawn together and, as discussed above, the present invention is not limited to any particular structure or methodology for drawing the two arms together. In this embodiment, stapling arm 150, and thus anvil arm 160, has a longitudinal axis $L_{SA}$ which extends generally parallel to the longitudinal axis $L_E$ of flexible endoscope 120 and of the flexible shaft.

Stapling head 152 and anvil head 162 will now be described in further detail. Stapling head 152 includes staples 156 that are arranged in parallel rows and staples 158 which are also arranged in parallel rows. Thus, stapling head 152 contains two sets of parallel rows of staples. Disposed between these sets of parallel rows of staples is a knife blade 154. Anvil head 162 includes complimentary anvil pockets 166, which align with each of the staples 156, and anvil pockets 168, which align with each of the staples 158. Thus, anvil pockets 166 are also arranged in a first set of parallel rows and anvil pockets 168 are also arranged in parallel rows. Thus, as can be understood, and as is well-known in the art, as the staples are driven from stapling head 152 the staples extend through tissue 170 where they then contact the anvil pockets to form the staples in their tissue retaining configuration. Anvil head 162 also contains a knife slot 164 which receives within it knife 154 when knife 154 is extended from stapling head 152 to cut the lesion that is to be removed from tissue 170.

Also included in stapling head 152 are staple drivers 156A and 158A and staple cams 156B and 158B. The staple drivers and staple cams can also be seen in FIG. 2, which will be discussed later in this specification. Staple drivers 156A and staple cam 156B are associated with the first set of staple rows and staple drivers 158A and staple cam 158B are associated with the second pair of staple rows. The purpose of the staples drivers and staple cams are to drive the staples from stapling head 152 during the resection procedure. The operation of the drivers and staple cams will be discussed when discussing FIG. 2.

In an embodiment, included on endoscope 120 is a stop 180. Stop 180 is disposed around endoscope 120 and extends from the outer periphery of endoscope 120. Stop 180 is disposed on endoscope 120 between staple arm 150 and anvil arm 160. Stop 180 restricts stapling arm 150 and anvil arm 160 from being extended too far beyond distal end 114 of closing cam 110. As can be understood, in this embodiment, as stapling arm 150 and anvil arm 160 are extended from distal end 114 of closing cam 110, eventually their structures will engage with stop 180 and will be restrained from further movement beyond stop 180. Thus, stop 180 provides for restraining stapling mechanism 140 from traveling over and beyond bending section 126 of flexible endoscope 120, which could damage bending section 126 of endoscope 120.

Stapling mechanism 140 should be sized such that the stapling arm 150 and anvil arm 160, and thus stapling head 152 and anvil head 162, can accommodate any of a variety of assemblies for the staple rows and knife edge. For example, stapling mechanism 140 is able to accommodate conventional open linear stapling devices. With conventional devices, a double staple row and knife has a total width of 4.5 millimeters. For reference purposes, the width direction is measured along an axis extending from the distal-most portion of stapling head 152 to its proximal-most portion as illustrated in FIG. 1 and which is, as will be discussed below for this embodiment, the transverse axis of stapling head 152. Other alternative known assemblies that may be utilized within stapling mechanism 140 are the conventional endoscopic linear stapling devices which could include an anvil with a thickness of 3.7 millimeters, a double staple line and knife width of 3.0 millimeters, a quadruple staple line and knife width of 5.8 millimeters, and a cartridge height for the staple lines and knife of 7.2 millimeters. Again, for reference purposes, the width $W_I$, anvil thickness $T_1$, and staple head height $H_1$ are illustrated in FIG. 1.

As can be further seen in FIG. 2, in this embodiment, stapling head 152 has a longitudinal axis $L_{SH}$ that is generally perpendicular to the longitudinal axis $L_{SA}$ of stapling arm 150 and also to the longitudinal axis $L_E$ of flexible endoscope 120.

Additionally, as can be seen in FIG. 1 and which will be a characteristic of all of the additional embodiments that will be discussed for the full-thickness resection system, grasper 130 is movable such that tissue 170 is pulled in a direction that is generally perpendicular to the longitudinal axis $L_{SH}$ of stapling head 152. It is desirable that the pulling direction of tissue 170 be perpendicular to the longitudinal axis of the stapling head in order to prevent wrinkling of the tissue at the edges of the linear stapling line. Additionally, a perpendicular pulling direction is desired because the gastric wall tissue 170 is generally thicker when contrasted with the thin-walled colon and thus a perpendicular pulling direction provides for greater mechanical advantage in pulling and maneuvering the thicker gastric wall. As can be seen in FIG. 3, gastric wall 172 generally has a thickness $T_{G1}$ of approximately 0.40–0.50 centimeters. A perpendicular pulling direction allows for more easily pulling the thicker-walled gastric tissue 172. As can be seen in FIG. 3, it is desirable that the pulled length of tissue 174 that is to be received within the stapling mechanism has a length $L_1$ of approximately 3 to 4 centimeters.

FIG. 2 is a front view of full-thickness resection system 100 and further illustrates stapling head 152 and anvil head 162. As can be seen in FIG. 2, and as was illustrated in FIG. 1, in this embodiment, flexible endoscope 120 is slidably received through the stapling mechanism 140. In further describing stapling head 152, it can be seen that the first row of aligned staples 156 is aligned on the longitudinal axis $L_{SH}$ of the stapling head 152. Any number of staples can be provided along this particular row and, more generally, any number of pairs of stapling rows can be utilized in the present invention. Whereas any number of pairs of rows may be utilized, it is desirable that at least one pair of rows is utilized with the positioning of the staples in each row staggered such that no gap will exist in the stapling line between the staples to provide for secure resectioning of the tissue.

Each staple 156 has a staple driver 156A associated with it. Staple drivers 156A are positioned directly above their associated staples and, when driven downwardly by staple cam 156B as will be described below, drives its associated staples from stapling head 152. Each driver 156A may be configured in any of a variety of configurations with one embodiment for driver 156A including a wedge-shaped cam surface 156AA as illustrated in FIG. 2.

In the embodiment of FIG. 2, staple cam 156B is formed as a sphere. Alternatively, the staple cam could be formed to include a wedge-shaped surface that is complementary in shape to the staple drivers. Staple cam 156B is pulled across each driver 156A by a cable 146. Cable 146 is attached at a first end 146A to staple cam 156B and is attached at a second end 146B to a first pulley 144 which rotates around a first axis. As will be described further when discussing FIGS. 4 and 5, an actuator 148 (not shown in FIG. 2 but visible as one embodiment in FIGS. 4 and 5) rotates first pulley 144 such that cable 146 is drawn around first pulley 144. As cable 146 is drawn around first pulley 144 as pulley 144 rotates about its axis, staple cam 156B is drawn across each driver 156A where staple cam 156B engages with each driver 156A and, due to the interaction of staple cam 156B and the wedge-shaped cam surface 156AA of each driver 156A, each driver is driven downwardly which fires its associated staples from stapling head 152. Thus, as staple cam 156B is drawn across each row of staples, the interaction of staple cam 156B with each driver 156A will drive each staple from stapling head 152. Whereas not illustrated in FIG. 2, stapling head 152 could include a channel which extends along the longitudinal axis of the stapling head within which staple cam 156B could be positioned. Provision of such a channel could assist in the alignment of staple cam 156B with respect to each of the drivers 156A. However, the provision of a channel within stapling head 152 is not required when practicing the present invention.

As can be further seen in FIG. 2, anvil head 162 includes an anvil pocket 166 that is associated with each staple 156, as described previously. Anvil head 162 has a width $W_2$ that is preferably approximately 18 millimeters. It is desirable that the width of anvil head 162, and thus, the width of stapling head 152, be approximately 18 millimeters or less in order so that the full-thickness resection system 100 can be inserted through a naturally occurring cavity of the body.

Whereas not specifically illustrated in FIG. 2, it can be understood that the third and fourth rows of staples and cam drivers as discussed when describing FIG. 1, would also have a staple cam 158B associated with them and would operate as described above.

FIGS. 4 and 5 illustrate a particular embodiment for an actuator 148 for rotating first pulley 144. FIG. 4 is a side view of the arrangement between actuator 148 and first pulley 144. In this embodiment, actuator 148 comprises a second pulley that rotates about its axis $P_2$. A second cable 149 extends proximally within full thickness resection system 100 and is attached at its first end 149A to second pulley 148. As second cable 149 is pulled proximally in the direction of the arrow in FIG. 4, second pulley 148 rotates about axis $P_2$. The rotation of pulley 148 about axis $P_2$ in-turn rotates first pulley 144 about its axis $P_1$. Second pulley 148 engages with first pulley 144 through interaction of gear teeth included on each of the pulleys. Thus, rotation of second pulley 148 about its axis $P_2$ in turn rotates first pulley 144 about axis $P_1$ where axis $P_2$ is perpendicular to axis $P_1$. As described previously, the rotation of first pulley 144 about axis $P_1$ draws cable 146 around first pulley 144 which in-turn draws the staple cams into engagement with the stapler drivers to drive the staples from the stapling head.

FIG. 5 provides a front view of first pulley 144 and actuator, or second pulley, 148. As can also be seen in FIG. 5, a positioning spring 147 can also be included within cable 146. The purpose of positioning spring 147 is to retain staple cam 156B in a position where it is not engaging with any of the drivers 156A before it is desired that staple cam 156B engage with drivers 156A. In the absence of a pulling force on cable 146, therefore, staples 156 cannot be accidentally fired from stapling head 152. When it is desired to fire staples 156 from stapling head 152, sufficient force is applied to cable 146 such that positioning spring 147 will elongate in order to allow staple cam 156B to be driven across drivers 156A. Thus, the utilization of a positioning spring can assist in ensuring that no staples are driven from stapling head 152 unless specifically acted upon by a user of the resectioning system.

As was mentioned previously, a variety of different structures could be utilized for actuator 148 in order to rotate first pulley 144 about its axis. An alternative embodiment for actuator 148 could be a rigid shaft that includes gear teeth on a distal end thereof that would engage with gear teeth that are included on first pulley 144. The shaft could be directly driven by a user of the system such as, for example, by rotating the shaft by utilizing the hand of the user. The direct rotation of the shaft would directly rotate first pulley 144 which in-turn would draw staple cam 156B across the drivers 156A. Thus, in this alternative embodiment, a second pulley would not be utilized to rotate first pulley 144, but rather, a directly-driven shaft would be utilized to rotate first pulley 144.

As mentioned previously, any of a variety of configurations can be utilized for grasper 130, and thus, grasping portion 132.

FIG. 6 illustrates a first embodiment for a grasping portion 132 that could be utilized in the present invention. In this embodiment, grasping portion 132 comprises a first arm 134 and a second arm 136. The first arm 134 and the second arm 136 are opposed from each other and are movable between an open position where tissue may be positioned between the arms and a tissue grasping position where the arms are drawn together such that they engage tissue 170 and are thus able to maneuver tissue 170 within the resection system.

FIG. 7 illustrates an alternative embodiment for a grasper 130 and grasping portion 132 that could be utilized with the present invention. In the embodiment of FIG. 7, grasping portion 132 comprises a T-shaped member. The T-shaped member is collapsed such that it has a generally flat configuration such that it may be inserted through the tissue 170 to an opposite side of tissue 170. Once the grasping portion 132 is positioned through tissue 170, the flexibly-configured T-shaped member springs into its T-shaped configuration such that as the grasping portion is drawn in the direction of the arrow illustrated in FIG. 7, the T-shaped member engages with the opposed side of tissue 170 such that tissue 170 may be drawn in the direction of the arrow in FIG. 7. A grasping portion configured in this alternative embodiment functions similar in fashion to a molley-type bolt as is utilized in different types of applications. T-shaped fasteners are known in the art and may be utilized in the present invention for grasping and positioning tissue within the resectioning system.

Whereas two particular embodiments for grasper 130 and grasping portion 132 have been described above, as stated previously, any other of a variety of contemplated devices could be practiced with the present invention for grasping tissue that is to be resectioned. Again, the present invention is not limited to any particular embodiment for grasper 130 and grasping portion 132.

A particular challenge in resectioning gastric tissue as opposed to resectioning tissue of tubular organs is that positioning and orienting of the resection device within the stomach can be much more difficult. In a tubular organ, the resectioning device may be inserted into the body cavity through the tubular organ, and thus, because the tubular organ is normally narrow in its configuration, the tubular organ itself serves to guide and orient the resectioning device within the organ. However, when utilizing a resectioning device within a large, open volume organ, such as the stomach, positioning and orienting of the resectioning device within that organ can be difficult. Whereas the device may be inserted into the patient's body through a tubular organ, such as the esophagus, once the resection device enters the stomach, the device is no longer constrained by the patient's body, but rather, is received within the large volume cavity of the stomach. As is illustrated in FIG. 8, therefore, a challenge exists in positioning and orienting resection device 100 within stomach 176 to accurately locate the distal end of resectioning device 100 at a location 178, for example, where tissue must be resectioned. The present invention may include a guide structure for assisting in the positioning of resection device 100 within an organ such as the stomach.

As can be seen in FIG. 9, an oversheath 120A is provided around flexible endoscope 120. FIG. 9 illustrates endoscope 120 without stapling mechanism 140 being included thereon. As was earlier described, flexible endoscope 120 includes a bending section 126 over which, it is not desirable that stapling mechanism 140 travel over. In order to assist in the positioning of stapling mechanism 140 at a difficult to access location within the stomach, a guide is included on oversheath 120A of endoscope 120 and recesses are provided within the elongated portion of the stapling mechanism such that the stapling mechanism may be guided along the guides that are included on the endoscope.

Figure 10:
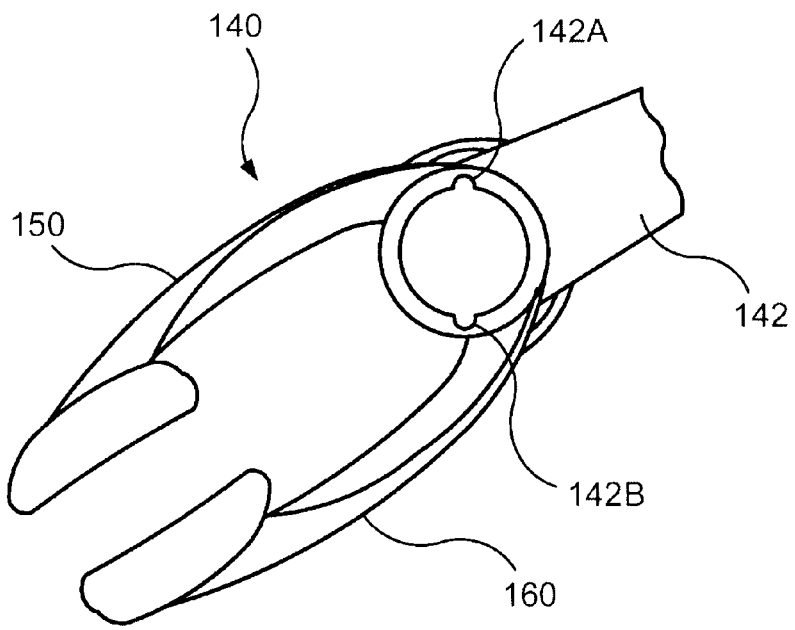
FIG. 10 illustrates an alternative embodiment for a stapling mechanism in accordance with the present invention.
Figure 11:
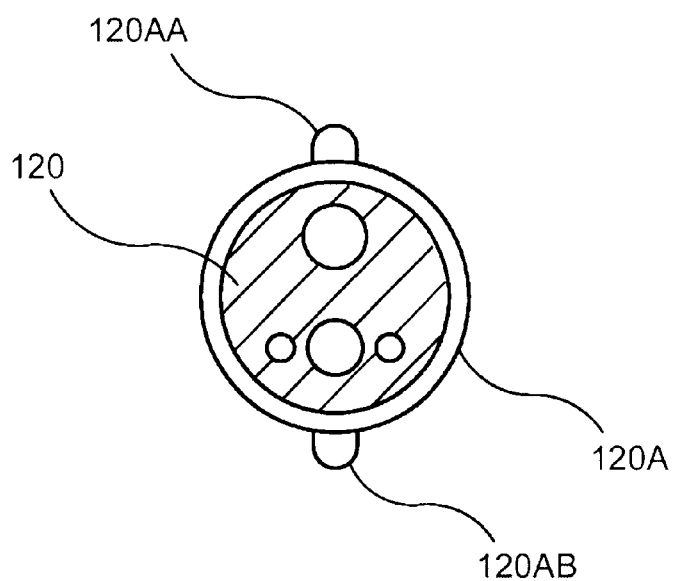
FIG. 11 is a front view of an alternative embodiment for an endoscope assembly in accordance with the present invention.

FIG. 10 illustrates an embodiment for stapling mechanism 140 that includes recesses that receive within them guides that are included on the oversheath of the endoscope. As can be seen in FIG. 10, elongated portion 142 of stapling mechanism 140 includes a first recess 142A and a second recess 142B that are defined by the interior surface of elongated portion 142. FIG. 11 illustrates oversheath 120A of endoscope 120 which includes a first guide rail 120AA and a second guide rail 120AB where both of the guide rails are disposed on the outer periphery of oversheath 120A and extend externally from the outer periphery. First guide rail 120AA is received within first recess 142A and second guide rail 120AB is received within second recess 142B. Thus, by positioning the first guide rail within the first recess and the second guide rail within the second recess, the relative positioning of the stapling mechanism 140 may be maintained on oversheath 120A and stapling mechanism 140 may be guided along oversheath 120A as the stapling mechanism 140 is moved on oversheath 120A when positioning stapling mechanism 140 at its desired location within the stomach. Thus, not only are the guide rails and recesses useful for guiding the stapling mechanism along the length of the oversheath but they are also useful in maintaining the relative position of the stapling mechanism with respect to the endoscope. For example, if the stapling mechanism 140 was not restrained against free rotation about oversheath 120A, the stapling arm 150 and anvil arm 160 may not be positioned properly with respect to the tissue to be resectioned when the stapling mechanism 140 is positioned at the lesion site.

Figure 12:
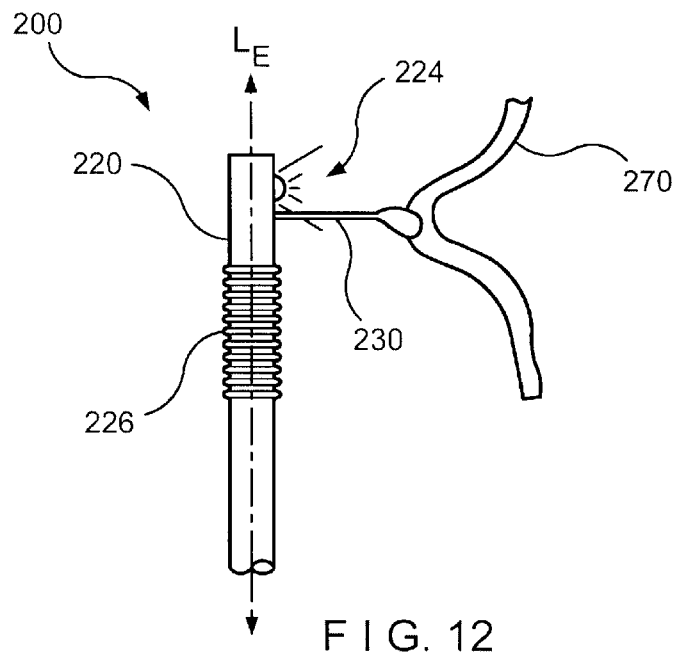
FIG. 12 illustrates an embodiment for a deuodenoscope in accordance with the present invention.
Figure 13:
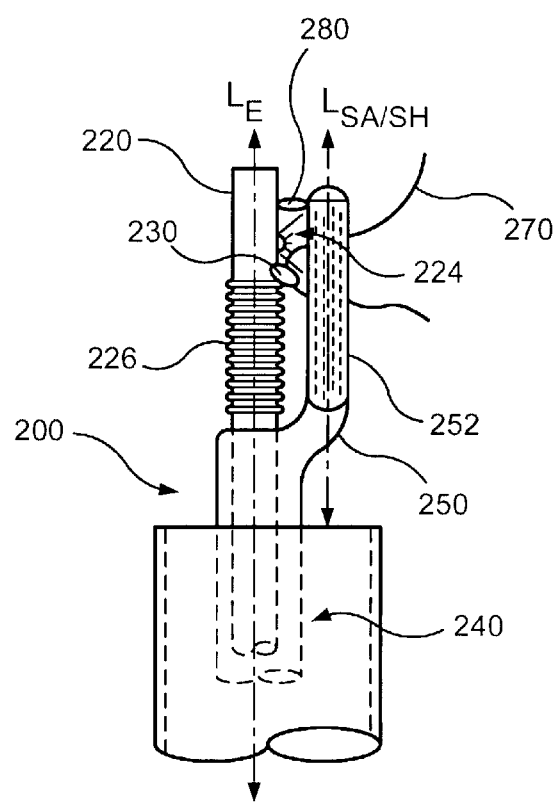
FIG. 13 illustrates a second embodiment for a full-thickness resection system in accordance with the present invention.

FIG. 12 illustrates an application where it is desirable that a grasper 230 grasps tissue 270 and pulls tissue 270 in a direction that is perpendicular to the longitudinal axis $L_E$ of the endoscope, which in this particular application, is more particularly defined as a deuodenoscope. Thus, in this embodiment for the endoscope, the deuodenoscope 220 may also include an optic 224 and a bending section 226. However, again, in this embodiment, the grasper 230 pulls the tissue 270 in a perpendicular direction to the longitudinal axis of the deuodenoscope, which is contrasted with the embodiment of FIG. 1 where the grasper 130 pulled the tissue in a direction that was parallel to the longitudinal axis of the endoscope 120. Thus, because the direction of pull of the tissue 270 is now perpendicular to the longitudinal axis of the deuodenoscope, it is not desirable that the stapling head be perpendicular to the longitudinal axis of the endoscope, as it was in the embodiment of FIG. 1, because if the longitudinal axis of the stapling head was perpendicular to the longitudinal axis of the deuodenoscope, the tissue 270 would be pulled by grasper 230 in a direction that would be parallel to the longitudinal axis of the stapling head, which is not desirable for the reasons discussed previously. Therefore, in this application where tissue 270 is pulled in a direction which is perpendicular to the longitudinal axis of the deuodenoscope, it is desirable that the longitudinal axis of the stapling head be parallel to the longitudinal axis of the deuodenoscope and the flexible shaft in which the deuodenoscope is disposed. In this configuration where the longitudinal axis of the stapling head 252 is parallel to the longitudinal axis of the deuodenoscope and the flexible shaft, as can be seen in FIG. 13, when the tissue 270 is pulled by the grasper 230, the tissue will not only be pulled in a direction perpendicular to the longitudinal axis of the deuodenoscope and flexible shaft but it will also be pulled in a direction which is perpendicular to the longitudinal axis of the stapling head, which is desirable as discussed previously. Thus, FIG. 13 illustrates a second embodiment for full-thickness resection system 200 where the longitudinal axis of the stapling head is now parallel to the longitudinal axis of the deuodenoscope and the flexible shaft.

As can be seen in FIG. 13, deuodenoscope 220 has a longitudinal axis $L_E$ and includes an optic 224 and a bending section 226. As discussed previously, a grasper 230 extends from deuodenoscope and is movable on an axis that is perpendicular to the longitudinal axis of the deuodenoscope. Thus, as described above, grasper 230 pulls tissue 270 in a direction that is perpendicular to the longitudinal axis of the deuodenoscope. As can also be seen in FIG. 13, a linear stapling mechanism 240 is attached to the scope oversheath of deuodenoscope 220. As in the previously discussed embodiment, stapling mechanism 240 includes a stapling arm 250 and an anvil arm (not visible in FIG. 13). Stapling arm 250 includes a stapling head 252. As can be seen in FIG. 13, both the longitudinal axis $L_{SA}$ of the stapling arm and the longitudinal axis $L_{SH}$ of the stapling head are parallel to the longitudinal axis $L_E$ of the deuodenoscope. Thus, as the tissue 270 is pulled within stapling mechanism 240 in a direction that is perpendicular to the longitudinal axis of the deuodenoscope, the tissue 270 is also pulled within stapling head 252 in a direction which is perpendicular to the longitudinal axis of the stapling head 252. Once the tissue 270 is drawn within stapling mechanism 240, the tissue may be resectioned by utilizing a knife blade and staples that are included within stapling mechanism 240, as described previously for the embodiment of FIG. 1. Thus, by providing a stapling head that has a longitudinal axis that is parallel with the longitudinal axis of the deuodenoscope, when the tissue 270 is pulled perpendicular to the longitudinal axis of the deuodenoscope, the tissue is also pulled within the stapling head in a perpendicular direction to the longitudinal axis of the stapling head. The embodiment of FIG. 13 provides a linear stapling mechanism 240 that can be utilized in an application where the tissue to be resectioned is pulled in a direction which is perpendicular to the longitudinal axis of the deuodenoscope.

In the embodiment of FIG. 13 for full-thickness resection system 200, it could be possible that, as a result of pulling tissue 270 perpendicular to the longitudinal axis of deuodenoscope 220, that the deuodenoscope 220 could be drawn within the stapling mechanism 240. Thus, it may be desirable to include a separator 280 that is disposed between the deuodenoscope 220 and the stapling head 252 of stapling mechanism 240. Separator 280 would engage with both deuodenoscope 220 and stapling head 252 to maintain separation between deuodenoscope 220 and stapling head 252, thus preventing the possibility that deuodenoscope 220 could be drawn within stapling head 252. Any of a variety of different configurations could be utilized for separator 280 and the present invention is not limited to any particular physical configuration. All that is required is that a structural member be included to maintain a separation distance between deuodenoscope 220 and stapling head 252. Separator 280 could be attached to either deuodenoscope 220 or stapling head 252.

In embodiments where the longitudinal axis of the stapling mechanism lies parallel to the longitudinal axis of the endoscope, and where a grasper does not extend perpendicular from the longitudinal axis of the endoscope, but rather extends along the longitudinal axis of the endoscope and extends from the distal end of the endoscope, challenges result in providing for pulling of the tissue within the stapling mechanism such that the tissue is pulled perpendicular to the longitudinal axis of the stapling mechanism, as is desired.

Figure 14:
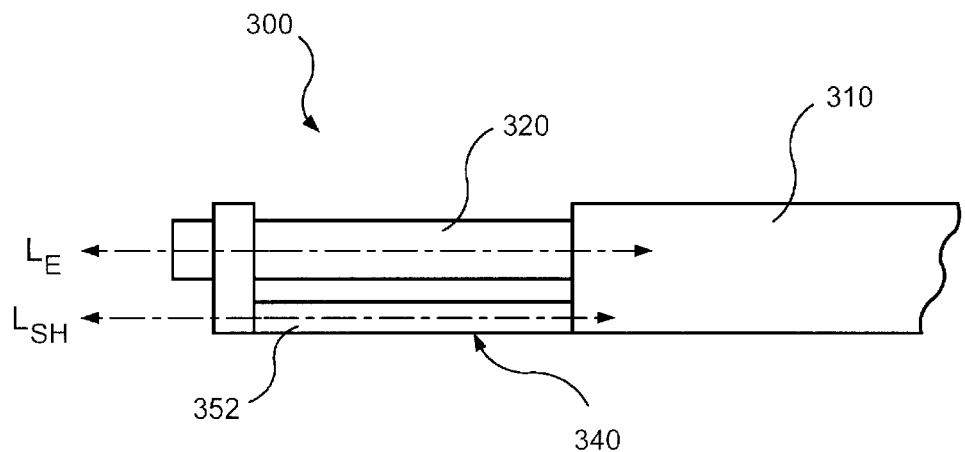
FIG. 14 illustrates a third embodiment for a full-thickness resection system in accordance with the present invention.
Figure 15:
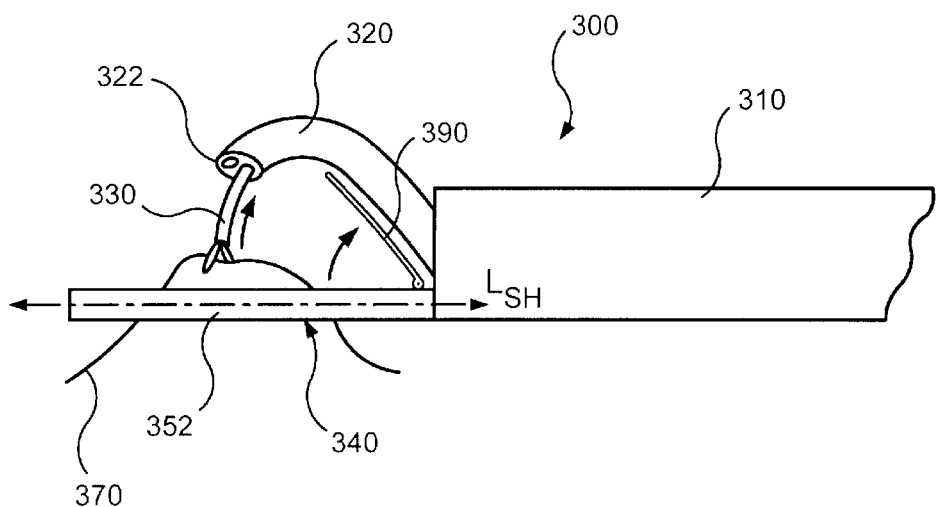
FIG. 15 illustrates the full-thickness resection system of FIG. 14 where an endoscope deflector has deflected the distal end of the endoscope.

FIGS. 14 and 15 illustrate a third embodiment for a full-thickness resection system 300 of the present invention that provides for perpendicular pulling of tissue within the stapling mechanism where the longitudinal axis of the stapling mechanism and the longitudinal axis of the endoscope are parallel.

As can be seen in FIG. 14, full-thickness resection system 300 includes a flexible shaft 310, a flexible endoscope 320, and a stapling mechanism 340. Flexible endoscope 320 has a longitudinal axis $L_E$ and stapling mechanism 340 has a longitudinal axis $L_{SH}$ which are parallel to each other. As discussed previously in the context of the other embodiments, stapling mechanism 340 includes a stapling head 352 and an anvil head (not visible in FIG. 14). Although not visible in FIG. 14, a grasper extends within a lumen included within flexible endoscope 320 and is movable on the longitudinal axis of flexible endoscope 320. Thus, the grasper extends from the distal end of the flexible endoscope 320 and is thus able to pull tissue in a direction that is parallel to the longitudinal axis of the flexible endoscope.

As is illustrated in FIG. 15, in order to position grasper 330 such that it is able to pull tissue 370 in a direction which is perpendicular to the longitudinal axis $L_{SH}$ of stapling mechanism 340, an endoscope deflector 390 is provided. Endoscope deflector 390 is pivotally attached to stapling mechanism 340 and is movable between a first position, where endoscope deflector 390 does not deflect the distal end 322 of endoscope 320, and a second position, where the endoscope deflector 390 deflects the distal end 322 of endoscope 320. When endoscope deflector 390 is pivoted to its second position the distal end 322 of endoscope 320 is moved such that it is no longer positioned on the longitudinal axis of endoscope 320. Rather, it is positioned such that, when grasper 330 extends from the distal end 322 of endoscope 320, grasper 330 is able to grasp tissue 370 and pull tissue 370 in a direction which is perpendicular to the longitudinal axis of stapling head 352 of stapling mechanism 340, as is desired. Thus, even in this configuration where the longitudinal axes of the endoscope and the stapling mechanism lie parallel to each other and where the grasper is movable along the longitudinal axis of endoscope 320, the distal end 322 of the endoscope 320 may be repositioned such that grasper 320 is able to perpendicularly pull tissue 370 within stapling head 352.

Any of a variety of different structures and methods may be utilized for moving endoscope deflector 390 into its first or second positions and the present invention is not limited to any particular structure or method. For example, a pull cable could be provided on endoscope deflector 390 that would extend proximally through flexible shaft 310. A user could simply pull on the pull cable to move endoscope deflector 390 to its second position. When the user releases the pulling force on the pull cable, a return biasing member could return endoscope deflector 390 to its first position. Other alternative embodiments can be contemplated and the present invention is not limited to any particular embodiment for actuating endoscope deflector 390.

Figure 16:
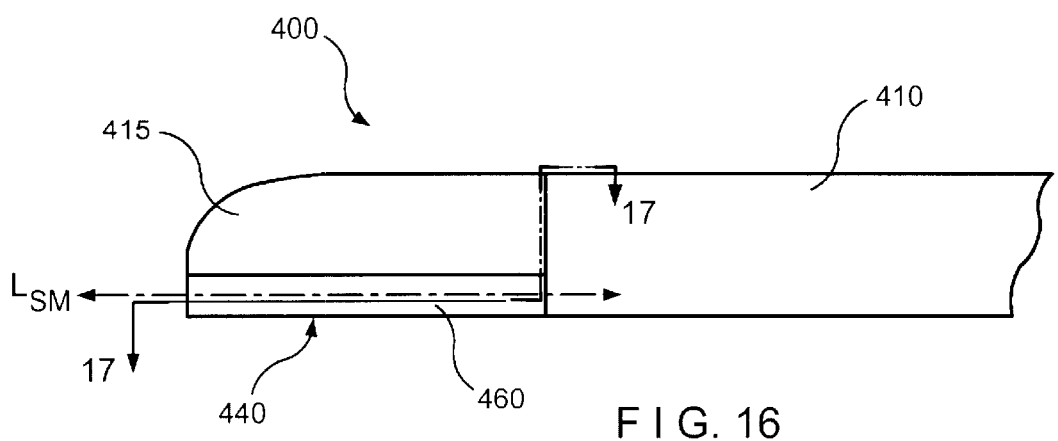
FIG. 16 illustrates a fourth embodiment for a full-thickness resection system in accordance with the present invention.
Figure 17:
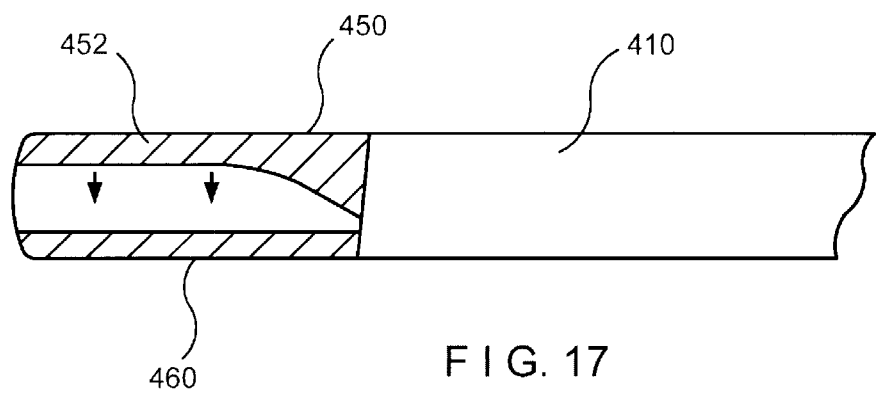
FIG. 17 is a cross-sectional view of the full-thickness resection system of FIG. 16 as taken along line 17—17 of FIG. 16.
Figure 18:
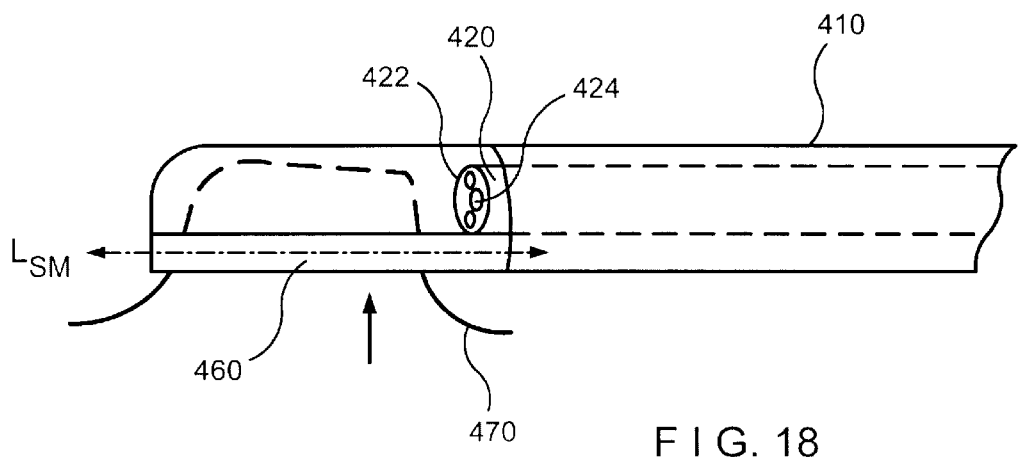
FIG. 18 illustrates the fill-thickness resection system of FIGS. 16 and 17 with tissue to be resected drawn into the resection system.

FIGS. 16 through 18 illustrate a fourth embodiment for a full-thickness resection system 400. The embodiment of FIGS. 16 through 18 also includes a stapling mechanism 440 that has a longitudinal axis $L_{SM}$ that is parallel to the longitudinal axis of an endoscope 420 which is included within flexible shaft 410. Thus, again, the challenge is presented for drawing tissue 470 in a direction that is perpendicular to the longitudinal axis of the stapling mechanism since the longitudinal axes of the stapling mechanism and the endoscope, and thus the flexible shaft 410, are parallel to each other. In further discussing the embodiment of FIGS. 16 through 18, stapling mechanism 440 includes an anvil arm 460 and a stapling arm 450 as discussed previously. Stapling arm 450 includes a stapling head 452. The longitudinal axis of stapling arm 450 is parallel to the longitudinal axis of stapling head 452. Attached to a distal end of flexible shaft 410 is a suction housing 415. Endoscope 420 includes a vacuum port 424 and distal end 422 of endoscope 420 is in barometric communication with suction housing 415, i.e., endoscope 420 is able to draw a vacuum on suction housing 415 through vacuum port 424. As can be seen in FIG. 18, when endoscope 420 draws a vacuum on suction housing 415, tissue 470 is drawn within suction housing 415 in a direction that is perpendicular to the longitudinal axis $L_{SM}$ of stapling mechanism 440. Thus, the embodiment of FIGS. 16 through 18 for full-thickness resection system 400 is able to draw tissue 470 perpendicular to the longitudinal axis of stapling head 452 by utilizing a suction to draw the tissue through the stapling head.

Whereas the above-described embodiment discusses an endoscope including a vacuum port having a distal end in barometric communication with the suction housing, it is not required to include an endoscope. Alternatively, a flexible suction catheter disposed through the flexible shaft could be utilized to draw a suction on the suction housing.

Figure 19:
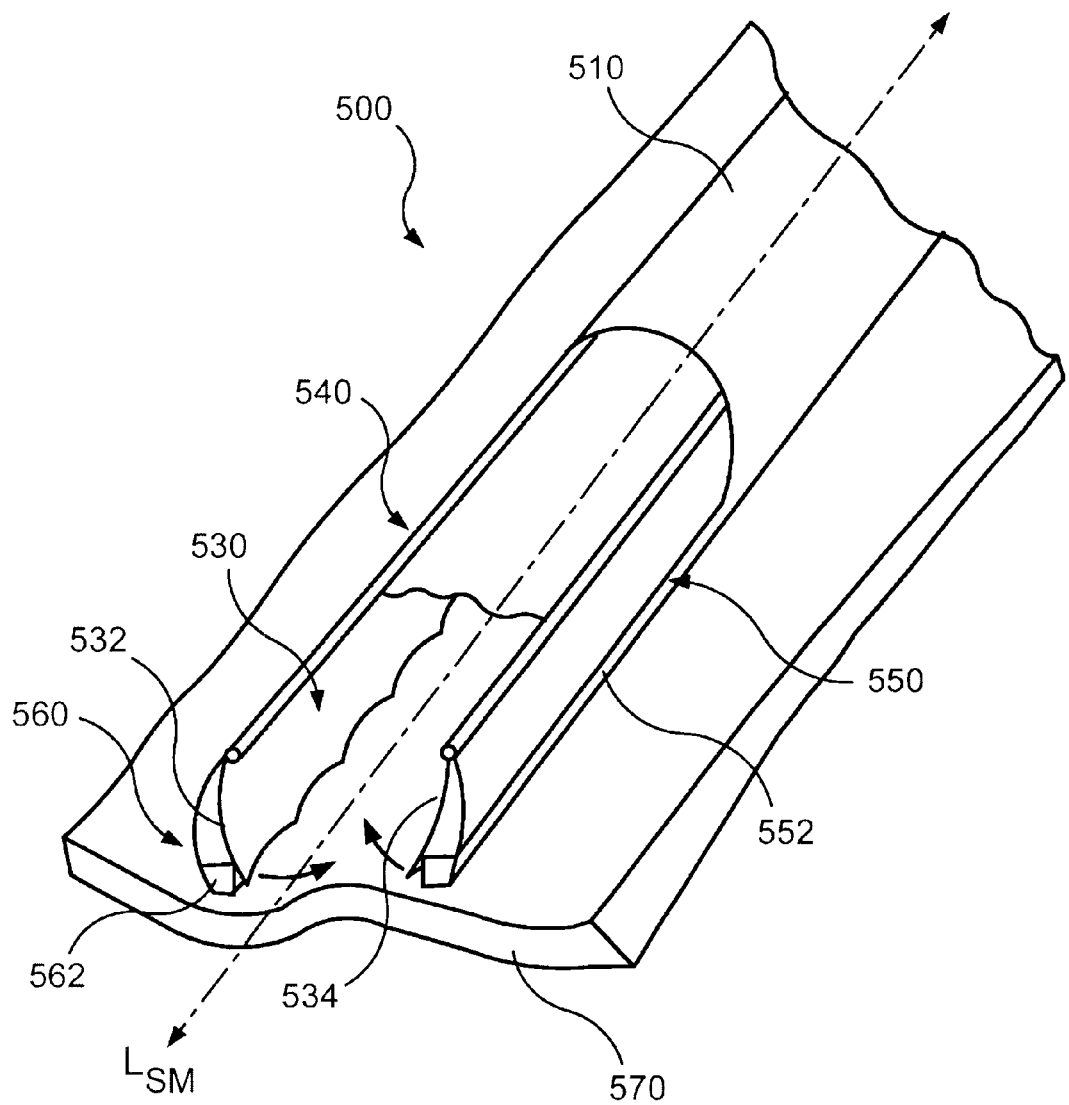
FIG. 19 illustrates a fifth embodiment for a full-thickness resection system in accordance with the present invention.

FIGS. 19 through 22 illustrate an alternative embodiment for full-thickness resection system 500 in an embodiment, again, where the longitudinal axis of the stapling mechanism 540 is parallel to the longitudinal axis of the flexible shaft 510 and the endoscope. As can be seen in FIG. 19, full-thickness resection system 500 includes a flexible shaft 510 through which an endoscope may extend (not illustrated in FIG. 19), as described earlier. Stapling mechanism 540 includes a stapling arm 550 and an anvil arm 560. Stapling arm 550 includes a stapling head 552 and anvil arm 560 includes an anvil head 562, as discussed previously. Again, stapling mechanism 540, and thus stapling head 552, has a longitudinal axis $L_{SM}$ which is parallel to the longitudinal axis of flexible shaft 510, and thus the longitudinal axis of the endoscope if contained within flexible shaft 510. Pivotally attached to an upper internal surface of stapling mechanism 540 is grasper 530 which includes a first wing 532 and a second wing 534. As stated above, each wing is pivotally attached to an upper internal surface of stapling mechanism 540 such that each wing may be pivoted in the directions as illustrated in FIGS. 19 through 22. As can be seen in FIG. 19, stapling mechanism 540 is positioned on a flat surface of tissue 570 which is to be resectioned. In order to perpendicularly pull tissue 570 between stapling arm 550 and anvil arm 560 of stapling mechanism 540, wings 532 and 534 are utilized.

As can be seen in FIG. 21, wing 532 is pivoted in the direction as shown and wing 534 is also pivoted in the direction as shown. Tissue 570 is grasped between the distal ends of wings 532 and 534 as the wings are pivoted towards each other. Continued pivoting of wings 532 and 534 in the directions as illustrated in FIG. 22 will further draw tissue 570 within stapling mechanism 540 and between stapling arm 550 and anvil arm 560. As can be seen in FIG. 22, the tissue 570 is drawn by wings 532 and 534 within stapling mechanism 540 in the direction that is perpendicular to the longitudinal axis of stapling mechanism 540. Once tissue 570 is drawn between stapling arm 550 and anvil arm 560 to the desired position, stapling arm 550 may be moved toward anvil arm 560 such that tissue 570 may be stapled and cut to remove the desired portion of tissue 570. Thus, in this additional embodiment where the staple head 552 of stapling mechanism 540 has a longitudinal axis which is parallel to the flexible shaft of the resection device, wings 532 and 534 are able to draw the tissue that is to be resectioned perpendicularly within stapling mechanism 540. Again, any variety of structures and methods may be utilized for pivoting wings 532 and 534 and the present invention is not limited to any particular structure or method. For example, a pull cable could be operably coupled to a pulley which is also operably coupled to a respective wing. By pulling on the cable, the pulley could be rotated which in-turn would pivot its respective wing. However, again, the present invention is not limited to any particular embodiment for pivoting wings 532, 534 and any of a variety of different structures and methods could be utilized.

In utilizing an embodiment of the present invention, the stapling mechanism is back loaded onto a flexible guide member, which in an embodiment may be an endoscope or gastroscope. The stapling mechanism is then retracted to a position proximal to the endoscope tip. The gastroscope is then moved through a naturally occurring body orifice, such as the mouth, into the body organ, e.g., the stomach, from which a lesion is to be removed. The distal end of the gastroscope is positioned proximate to the lesion that is to be removed from the organ. The tissue specimen that contains that lesion is grasped using the grasper mechanism that is included within a lumen in the endoscope. Again, the grasper may be any of a variety of grasper mechanisms. After grasping the tissue specimen with the grasper to stabilize the position of the endoscope, the stapling mechanism is advanced into position using the endoscope as a guidewire. In order to facilitate passage of the stapling mechanism through the esophagus, the stapling head and the anvil head are drawn together to facilitate their passage through the esophagus. Once the stomach is reached by the stapling mechanism, the stapling head and the anvil head are opened to their tissue receiving position. The endoscope position may need to be adjusted so that the view of the lesion to be resectioned is optimized for the physician performing the operation. Retraction of the gastric wall brings the lesion into the stapling mechanism and thus between the stapling head and the anvil head of the stapling mechanism. The stapling head and the anvil head are then drawn together to compress the gastric wall. The stapling mechanism is actuated to form the approximating wound closure. Subsequently, the cutting knife is moved through the clamped stapled tissue to complete the resection. The stapling mechanism's stapling head and anvil head are then opened and the treatment site is inspected with the endoscope. After inspection, assuming all is satisfactory, the staple head and anvil head are then again drawn together for removal from the patient through the esophagus. The tissue specimen is retained by the grasping device and is withdrawn from the organ as the device and endoscope are removed from the patient.

If an endoscope is not utilized in the present invention, visualization of the subject area can be obtained by utilizing an endoscope separate from the full-thickness resection device of the present invention. Optionally, as discussed previously, the stapling mechanism can be loaded onto a flexible guide member disposed within the flexible shaft. Additionally, any of the components described herein that are associated with an endoscope, such as the closing cams discussed below and a stop as discussed previously, can be associated with the flexible guide member.

As was discussed earlier in this specification, alternative embodiments for effecting relative movement between the closing cam and the staple arm and anvil arm in order to pivot the arms to clamp tissue between the arms and provide a controlled staple gap between the arms are contemplated. For example, a movable closing cam can be utilized such that it can be moved relative to the arms by utilizing gears, pull cable(s)/pulley(s), and hydraulics. Other mechanisms are also within the scope of the present invention that are capable of producing linear translation of the closing cam. All that is required is that the closing cam and arms move relative to each other. Again, this can be accomplished by either moving the arms such that they are retracted into and extended from the closing cam or by moving the closing cam such that it linearly translates with respect to the arms.

Figure 23:
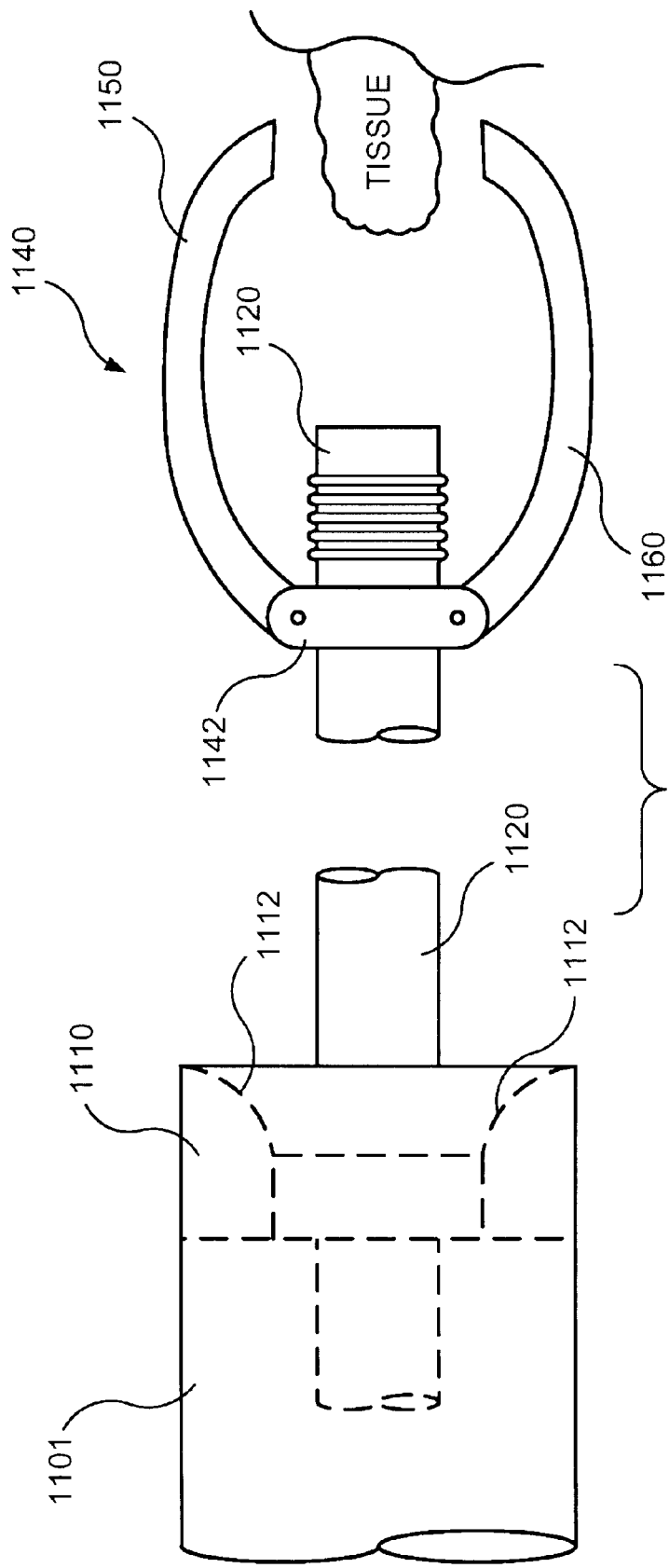
FIG. 23 is an illustration of a closing cam and stapling mechanism in accordance with the principles of the present invention.

As illustrated in FIG. 23, a full-thickness resection system in accordance with the principles of the present invention and which may include all of the features as described previously in the other embodiments is disclosed. The resection device of FIG. 23 only illustrates those features which help to illustrate the alternative embodiments for a movable closing cam and for actuating the closing cam, however, as discussed above, the embodiment of FIG. 23 is not limited to only the illustrated features. The resection system of FIG. 23 includes a movable closing cam, or camming ring 1110, which may be included within flexible shaft 1101 or movable on shaft 1101, a flexible endoscope 1120, and a stapling mechanism 1140. Stapling mechanism 1140 includes stapling arm 1150 and anvil arm 1160, as described previously. Stapling mechanism 1140 also includes stapler attachment mechanism 1142 and arms 1150, 1160 are pivotally attached to attachment mechanism 1142. Camming ring 1110 includes camming surfaces 1112 which are engageable with arms 1150, 1160 to pivot the arms closed in order to clamp tissue between them and to provide a controlled staple gap. As stated above, in this embodiment and the embodiments of FIGS. 24–27, which will be discussed below, camming ring 1110 moves either within or on flexible shaft 1101 to engage with stapling mechanism 1140. A closing cam actuating device (not shown in FIG. 23) is utilized to move camming ring 1110. In FIGS. 23–27 similar components are designated by similar reference numerals. As was also stated above, the embodiments of FIGS. 23–27 may also include any of the other features of this invention that were described previously in this specification in connection with the other embodiments disclosed.

Figure 25:
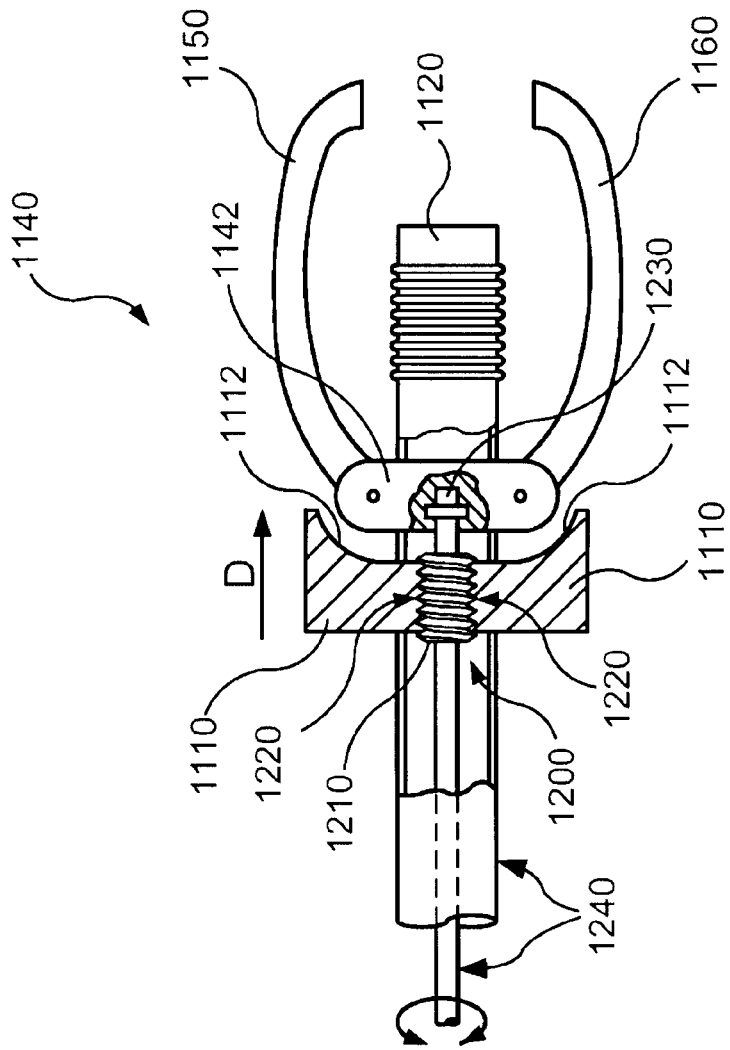
FIG. 25 illustrates the closing cam actuating device of FIG. 24.

FIGS. 24 and 25 illustrate a first embodiment for a closing cam actuating device in accordance with the principles of the present invention. Closing cam actuating device 1200 includes a worm gear 1210, a rack 1220, a worm gear shaft 1230, and a flexible drive cable 1240. The rack 1220 may be integrally included on camming ring 1110 and is threaded such that it threadedly mates with threaded worm gear 1210. Worm gear shaft 1230 is attached to worm gear 1210 at a first end and pinned to stapler attachment member 1142 at a second end. Flexible drive cable 1240 is attached to worm gear 1210.

Rotation of flexible drive cable 1240 causes worm gear 1210 to rotate. Rotation of worm gear 1210, which is mated with rack 1220, causes the camming ring 1110 to move forward in the direction of the arrow D in FIG. 25 such that camming surfaces 1112 contact arms 1150, 1160 of stapling mechanism 1140 causing the arms to pivot, and thus, close about stapler attachment member 1142 to clamp tissue between them and to provide a controlled staple gap.

Figure 26:
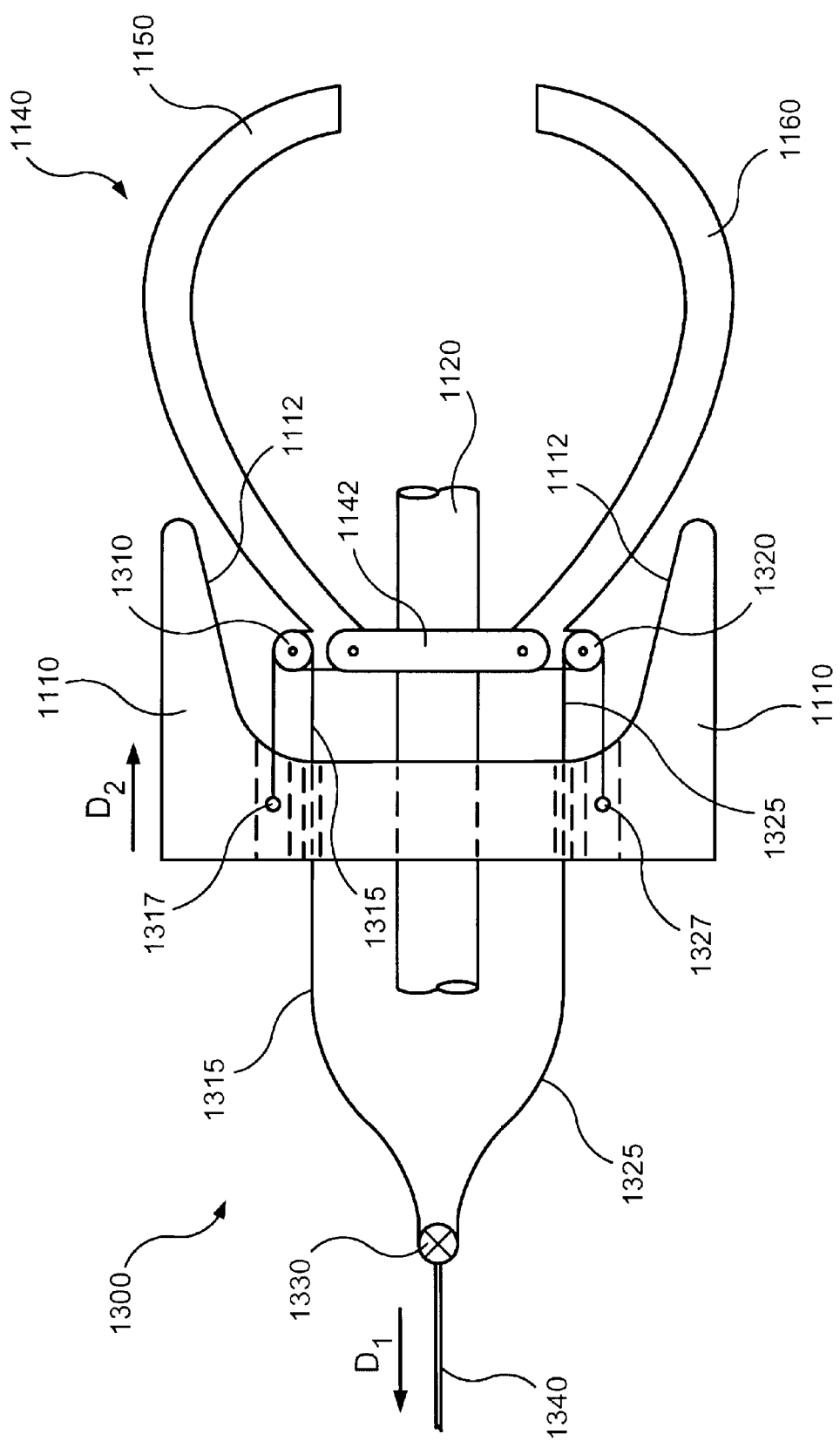
FIG. 26 illustrates a second alternative embodiment of a closing cam actuating device.

FIG. 26 illustrates a second embodiment for a closing cam actuating device in accordance with the principles of the present invention. Closing cam actuating device 1300 includes a first pulley 1310, a second pulley 1320, a first cable 1315, a second cable 1325, and a pull wire 1340. The first and second pulleys 1310, 1320 are included on opposite ends of stapler attachment member 1142. First cable 1315 is rigidly attached at a first end 1317 to camming ring 1110 and extends around first pulley 1310 and through camming ring 1110 to attachment point 1330. Second cable 1325 is rigidly attached at a first end 1327 to camming ring 1110 and extends around second pulley 1320 and through camming ring 1110 to attachment point 1330. Apertures are provided in camming ring 1110 to provide for passage of the first and second cables through the camming ring. Pull wire 1340 is also attached to attachment point 1330 and runs outside of a scope insertion tube. Whereas two cables and two pulleys are disclosed in this embodiment, it is not required that two of each of these components be utilized in the present invention. It is possible to actuate the camming ring by only utilizing one cable and one pulley, both of which would be more centrally positioned with respect to the camming ring and the stapler attachment member.

As can be understood, pulling of pull wire 1340 by an operator in the direction of the arrow $D_1$ causes the camming ring 1110 to move forward in the direction of the arrow $D_2$ in FIG. 26 such that camming surfaces 1112 contact arms 1150, 1160 of stapling mechanism 1140 causing the arms to pivot, and thus, close about stapler attachment member 1142.

Figure 27:
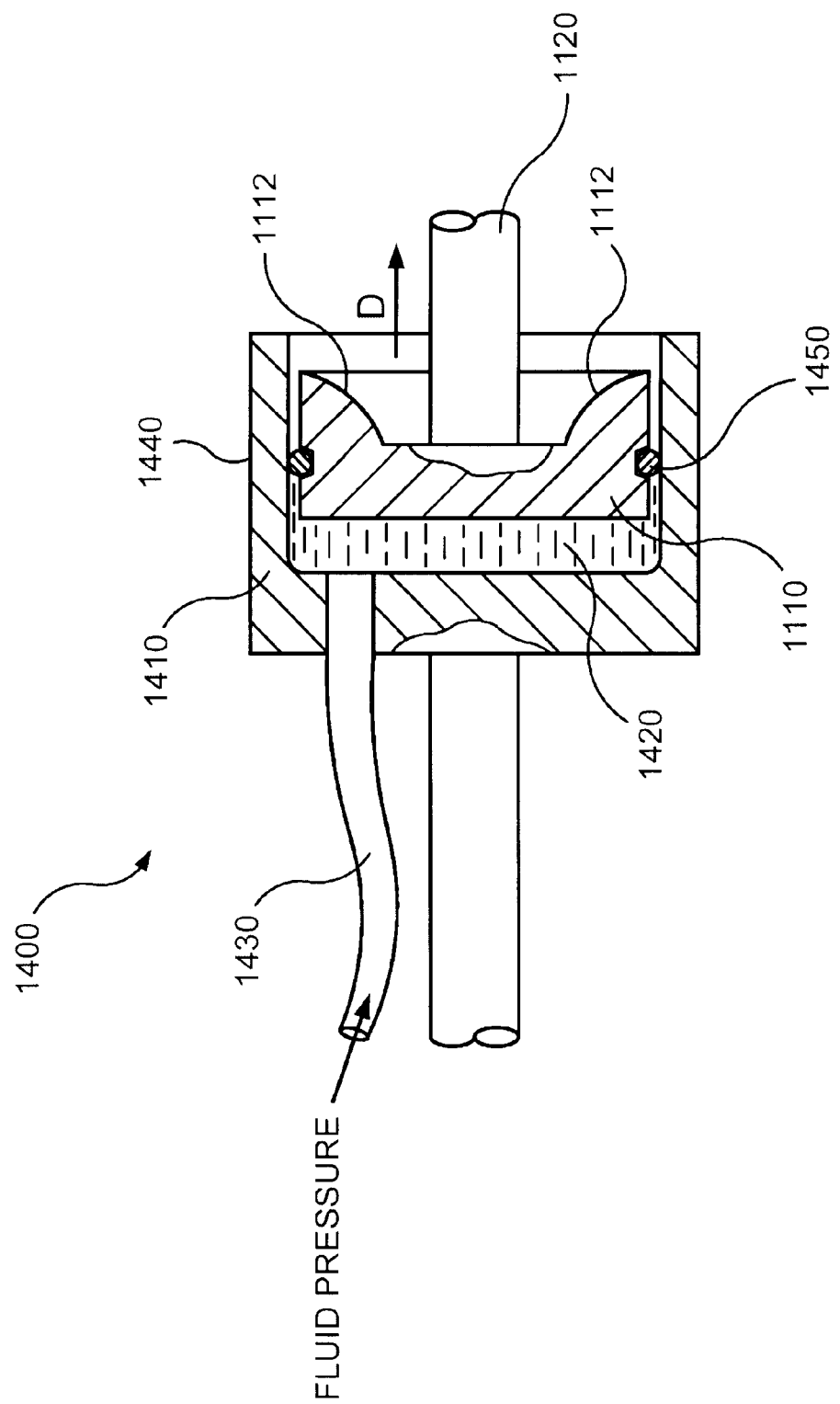
FIG. 27 illustrates a third alternative embodiment of a closing cam actuating device.

FIG. 27 illustrates a third embodiment for a closing cam actuating device in accordance with the principles of the present invention. Closing cam actuating device 1400 includes a fluid reservoir base 1410, a fluid reservoir cavity 1420, a fluid supply line 1430, and first and second hydraulic seals 1440,1450, respectively. Fluid reservoir base 1410 surrounds flexible endoscope 1120. Camming ring 1110 is received within fluid reservoir base 1410. Fluid reservoir base 1410, camming ring 1110 and first and second hydraulic seals 1440, 1450 together form fluid reservoir cavity 1420. Fluid supply line 1430 supplies fluid to fluid reservoir cavity 1420. The reservoir base may be attached to the stapler attachment member via a rigid, annular tube (not shown).

As can be understood, pressurization of fluid reservoir cavity 1420 by pumping or forcing fluid into the fluid reservoir cavity 1420 causes the camming ring 1110 to act as a piston and, thus, causes the camming ring 1110 to be translated forward in the direction of the arrow D in FIG. 27 such that camming surfaces 1112 contact the arms of the stapling mechanism which causes the arms to pivot, and thus, close about the stapler attachment member. The camming ring 1110 can be biased into its retracted position such that when the fluid pressure in fluid reservoir cavity 1420 is reduced, the camming ring will return to its retracted position where it no longer engages with the stapling mechanism.

Any of the disclosed embodiments for a full-thickness resection system can utilize any of the disclosed mechanisms and methodologies for actuating the arms of the stapling mechanism. Additionally, any of a variety of other known mechanisms and methodologies can be utilized in the present invention. All that is required is that the arms of the stapling mechanism be actuated to clamp tissue and provide a controlled staple gap.

The disclosed embodiments are illustrative of the various ways in which the present invention may be practiced. Other embodiments can be implemented by those skilled in the art without departing from the spirit and scope of the present invention.

What is claimed is:

1. A full-thickness resection system for removing a full-thickness portion of a body organ, the system comprising:
   a flexible shaft having a longitudinal axis;
   a flexible guide member having a longitudinal axis disposed within said flexible shaft and having a distal end extendable beyond a distal end of said flexible shaft;
   a stapling mechanism having an elongated portion at least partially disposed within said flexible shaft and disposed around said flexible guide member and including:
      a stapling arm having a longitudinal axis, said stapling arm including a stapling head having a longitudinal axis; and
      an anvil arm having an anvil head;
      wherein said stapling arm and said anvil arm extend from said elongated portion and are moveable with respect to each other between a tissue receiving position and a stapling position; and
   a grasper, said grasper extending through said flexible shaft and adapted to grasp a portion of a tissue to be excised from the body organ, said grasper movable on an axis perpendicular to said longitudinal axis of said stapling head.

2. The full-thickness resection system of claim 1 wherein said flexible guide member is a flexible endoscope and wherein said grasper extends through a lumen included within said flexible endoscope.

3. The full-thickness resection system of claim 2 wherein said endoscope includes a guide member disposed on an outer periphery of said endoscope and extending externally from said outer periphery of said endoscope and wherein said elongated portion of said stapling mechanism defines a recess therein, said guide member received within said recess.

4. The full-thickness resection system of claim 2 further comprising a closing cam, said closing cam movably disposed around said flexible endoscope and engageable with said stapling mechanism.

5. The full-thickness resection system of claim 4 further comprising a closing cam actuating device, said closing cam movably coupled to said closing cam actuating device, said closing cam actuating device including:
   a worm gear;
   a rack disposed on said closing cam and threadedly engageable with said worm gear;
   a worm gear shaft attached at a first end to a first end of said worm gear and attached at a second end to said stapling mechanism; and
   a drive cable attached to said worm gear at a second end of said worm gear.

6. The full-thickness resection system of claim 4 further comprising a closing cam actuating device, said closing cam movably coupled to said closing cam actuating device, said closing cam actuating device including:
   a pulley attached to said stapling mechanism;
   a cable, said cable attached to said closing cam at a first end of said cable and disposed around said pulley; and
   a pull wire attached to said cable at a second end of said cable.

7. The full-thickness resection system of claim 4 further comprising a closing cam actuating device, said closing cam movably coupled to said closing cam actuating device, said closing cam actuating device including:
   a fluid reservoir base sealingly coupled to said closing cam;
   a fluid reservoir cavity defined by said fluid reservoir base and said closing cam; and
   a fluid supply line in fluid communication with said fluid reservoir cavity.

8. The full-thickness resection system of claim 1 wherein said grasper is a suction catheter.

9. The full-thickness resection system of claim 1 wherein said stapling mechanism includes a plurality of staple drivers each having a wedge-shaped cam surface on a top end thereof and a staple cam movable such that said staple cam contacts each of said plurality of staple drivers to drive a plurality of staples from said stapling head.

10. The full-thickness resection system of claim 9 wherein said stapling mechanism further includes:
    a pulley rotatable around a first axis;
    a first cable attached at a first end to said staple cam and at a second end to said pulley; and
    an actuator in operable engagement with said pulley to rotate said pulley around said first axis.

11. The full-thickness resection system of claim 10 wherein said actuator includes:
    a second pulley rotatable around a second axis, said second axis perpendicular to said first axis; and
    a second cable attached at a first end to said second pulley.

12. The full-thickness resection system of claim 10 wherein said actuator includes a shaft including gear teeth on a distal end thereof, said gear teeth engaging with gear teeth included on said first pulley.

13. The full-thickness resection system of claim 9 wherein said staple cam is formed as a sphere.

14. The full-thickness resection system of claim 9 wherein said staple cam includes a wedge-shaped surface.

15. The full-thickness resection system of claim 9 wherein said stapling head defines a channel and wherein said staple cam is disposed within said channel.

16. The full-thickness resection system of claim 1 wherein said longitudinal axis of said stapling arm is parallel to said longitudinal axis of said flexible shaft and wherein said longitudinal axis of said stapling head is perpendicular to said longitudinal axis of said stapling arm.

17. The full-thickness resection system of claim 1 wherein said longitudinal axis of said stapling arm is parallel to said longitudinal axis of said flexible shaft and wherein said longitudinal axis of said stapling head is parallel to said longitudinal axis of said stapling arm.

18. The full-thickness resection system of claim 17 wherein said flexible guide member is a flexible endoscope and further comprising a separation member disposed between and engaging with said endoscope and said stapling mechanism.

19. The full-thickness resection system of claim 17 wherein said flexible guide member is a flexible endoscope and wherein said grasper extends through a lumen included within said flexible endoscope and further comprising an endoscope deflector pivotally attached to said stapling mechanism and movable between a first position where said endoscope deflector does not deflect said endoscope and a second position where said endoscope deflector deflects said distal portion of said endoscope such that said distal portion is not aligned with said longitudinal axis of said endoscope.

20. The full-thickness resection system of claim 1 further including a stop member wherein said stop member is disposed around said flexible guide member and extends from an outer periphery of said flexible guide member and wherein said stop member is disposed between said staple arm and said anvil arm.

21. The full-thickness resection system of claim 1 wherein said grasper includes a pair of opposed arms movable between a tissue grasping position and an open position.

22. The full-thickness resection system of claim 1 wherein said grasper is a T-shaped member.

23. The full-thickness resection system of claim 1 further comprising a closing cam, said closing cam included on a distal end of said flexible shaft.

24. A full-thickness resection system for removing a full-thickness portion of a body organ, the system comprising:
  a flexible shaft including a suction housing disposed on a distal end thereof;
  a flexible suction catheter disposed though said flexible shaft and including a distal end in barometric communication with said suction housing; and
  a stapling mechanism having a longitudinal axis and disposed though said flexible shaft and including a stapling arm and an anvil arm both of which are extendable beyond a distal end of said flexible shaft;
  wherein said stapling arm and said anvil arm are moveable with respect to each other between a tissue receiving position and a stapling position and wherein a vacuum is drawn by said flexible suction catheter on said suction housing, said vacuum capable of drawing a portion of a tissue to be excised from the body organ between said stapling arm and said anvil arm on an axis perpendicular to said longitudinal axis of said stapling mechanism.

25. The full-thickness resection system of claim 24 wherein said flexible suction catheter is disposed within a flexible endoscope.

26. A full-thickness resection system for removing a full-thickness portion of a body organ, the system comprising:
  a flexible shaft; and
  a stapling mechanism having a longitudinal axis and disposed though said flexible shaft and including:
    a stapling arm extendable beyond a distal end of said flexible shaft;
    an anvil arm extendable beyond said distal end of said flexible shaft; and
    a pair of graspers pivotally attached to an internal surface of said stapling mechanism;
  wherein said stapling arm and said anvil arm are moveable with respect to each other between a tissue receiving position and a stapling position and wherein said pair of graspers are adapted to draw a portion of a tissue to be excised from the body organ between said stapling arm and said anvil arm on an axis perpendicular to said longitudinal axis of said stapling mechanism.

27. The full-thickness resection system of claim 26 further comprising a flexible endoscope disposed within said flexible shaft and having a distal end extendable beyond said distal end of said flexible shaft.

* * * * *